United States Patent [19]

Jenkins et al.

[11] Patent Number: 5,981,545
[45] Date of Patent: Nov. 9, 1999

[54] N-LINKED AZABICYCLIC HETEROCYCLES USEFUL FOR TREATING DEMENTIA

[75] Inventors: Sarah Margaret Jenkins; Harry John Wadsworth; Barry Sidney Orlek; Steven Mark Bromidge, all of Harlow, United Kingdom

[73] Assignee: Beecham Group p.l.c., Middlesex, United Kingdom

[21] Appl. No.: 07/594,034

[22] Filed: Oct. 4, 1990

[30] Foreign Application Priority Data

Oct. 7, 1989 [GB] United Kingdom .................. 8922620
Jul. 21, 1990 [GB] United Kingdom .................. 9016069

[51] Int. Cl.⁶ .................. A61K 31/41; A61K 31/435; C07D 221/22; C07D 453/02
[52] U.S. Cl. .................. 514/299; 514/305; 514/381; 546/112; 546/133; 548/250
[58] Field of Search .................. 546/133, 112; 514/305, 299, 381; 548/250

[56] References Cited

U.S. PATENT DOCUMENTS

| | | | |
|---|---|---|---|
| 3,813,384 | 5/1974 | Vogelsang et al. | 540/599 |
| 4,224,332 | 9/1980 | Gueremy et al. | 546/133 X |
| 4,968,691 | 11/1990 | Orlek | 546/133 X |
| 5,200,419 | 4/1993 | Hobbs et al. | 514/323 |

FOREIGN PATENT DOCUMENTS

| | | |
|---|---|---|
| 287356 | of 0000 | European Pat. Off. . |
| 0239309 | 9/1987 | European Pat. Off. . |
| 0296721 | 12/1988 | European Pat. Off. . |
| 0301729 | 2/1989 | European Pat. Off. . |
| 0307140 | 3/1989 | European Pat. Off. . |
| 0307141 | 3/1989 | European Pat. Off. . |
| 0307142 | 3/1989 | European Pat. Off. . |
| 0316718 | 5/1989 | European Pat. Off. . |
| 0322182 | 6/1989 | European Pat. Off. . |
| 0323864 | 7/1989 | European Pat. Off. . |
| 0339834 | 11/1989 | European Pat. Off. . |
| 0363085 | 4/1990 | European Pat. Off. . |
| 0366304 | 5/1990 | European Pat. Off. . |
| 0375450 | 6/1990 | European Pat. Off. . |
| 0402056 | 12/1990 | European Pat. Off. . |

Primary Examiner—Shean C. Wu
Attorney, Agent, or Firm—Hopgood, Calimafde, Kalil & Judlowe

[57] ABSTRACT

A compound of formula (I) or a pharmaceutically acceptable salt thereof:

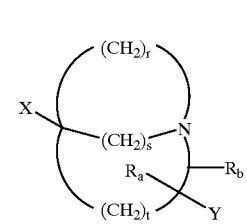

(I)

in which one of X and Y represents hydrogen and the other represents Z, where Z is a group

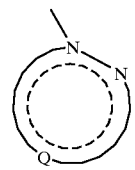

in which Q represents a 3-membered divalent residue completing a 5-membered aromatic ring and comprises zero, one or two nitrogen atoms, Q being optionally C-substituted by a group $R_1$ selected from halogen, CN, $OR_2$, $SR_2$, $N(R_2)_2$, $NHCOR_2$, $NHCOOCH_3$, $NHCOOC_2H_5$, $NHOR_2$, $N_3$, $NHNH_2$, $NO_2$, $COR_2$, $COR_3$, $C_{2-4}$ alkenyl, $C_{2-4}$ alkynyl, cyclopropyl or $C_{1-2}$ alkyl optionally substituted with $OR_2$, $N(R_2)_2$, $SR_2$, $CO_2R_2$, $CON(R_2)_2$ or one, two or three halogen atoms, in which each $R_2$ is independently hydrogen or $C_{1-2}$ alkyl and $R_3$ is $OR_2$, $NH_2$ or $NHR_2$; r represents an integer of 2 or 3, s represents an integer of 1 or 2 and t represents 0 or 1; $R_a$ and $R_b$ each represent hydrogen or, when X is hydrogen, optionally together represent a bond; with the proviso that when Y is hydrogen s is 1.

8 Claims, No Drawings

N-LINKED AZABICYCLIC HETEROCYCLES USEFUL FOR TREATING DEMENTIA

This invention relates to compounds having pharmaceutical activity, to a process for their preparation and their use as pharmaceuticals.

EP-A-0261763 and EP-A-0287356 disclose certain non-aromatic 1-azabicyclic ring systems substituted by certain 5-membered aromatic heterocycles.

A novel group of compounds has now been discovered which enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

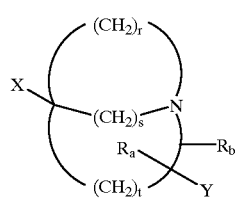

(I)

in which one of X and Y represents hydrogen and the other represents Z, where Z is a group

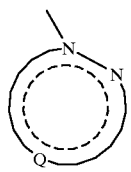

in which Q represents a 3-membered divalent residue completing a 5-membered aromatic ring and comprises zero, one or two nitrogen atoms, Q being optionally C-substituted by a group $R_1$ selected from halogen, CN, $OR_2$, $SR_2$, $N(R_2)_2$, $NHCOR_2$, $NHCOOCH_3$, $NHCOOC_2H_5$, $NHOR_2$, $N_3$, $NHNH_2$, $NO_2$, $COR_2$, $COR_3$, $C_{2-4}$ alkenyl, $C_{2-4}$ alkynyl, cyclopropyl or $C_{1-2}$ alkyl optionally substituted with $OR_2$, $N(R_2)_2$, $SR_2$, $CO_2R_2$, $CON(R_2)_2$ or one, two or three halogen atoms, in which each $R_2$ is independently hydrogen or $C_{1-2}$ alkyl and $R_3$ is $OR_2$, $NH_2$ or $NHR_2$; r represents an integer of 2 or 3, s represents an integer of 1 or 2 and t represents 0 or 1; $R_a$ and $R_b$ each represent hydrogen or, when X is hydrogen, optionally together represent a bond; with the proviso that when Y is hydrogen s is 1.

Certain compounds of formula (I) are capable of existing in a number of stereoisomeric forms including enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

In compounds of formula (I) having two assymmetric centres where Y is other than hydrogen and $R_a$ and $R_b$ each represent hydrogen, the stereo-chemical configuration in which the group Y and the $(CH_2)s$ bridge are on the same side of the plane of the molecule which contains both bridgehead atoms and the ring carbon atom bonded to the group Y will herein be referred to as the exo configuration. Similarly, the configuration of compounds in which the group Y and the bridge $(CH_2)s$ are on opposite sides of the above-mentioned plane of the molecule will herein be referred to as the endo configuration. Preferably compounds of formula (1) have the exo configuration.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

Preferred combinations of (r, s, t) include (2,2,0), (3,1,0), (2,1,0), (2,1,1) and (3,1,1). Examples of combinations of (r, s, t) include (2,2,0), (3,1,0) and (2,1,0).

Halogen in $R_1$ includes fluoro, chloro, bromo and iodo.

The substituent $R_1$ on Z is preferably y to the position of the azabicyclic ring.

Examples of $R_1$ include hydrogen, methyl, ethyl, amino, nitro, azido, cyano, chloro, bromo and iodo, preferably hydrogen, methyl and amino.

5-Membered aromatic heterocycles within the definition of variable Z include 1,2-pyrazol-1-yl, 1,2,4-triazol-1-yl, 1,2,3-triazol-1-yl, 1,2,3-triazol-2-yl, tetrazol-1-yl and tetrazol-2-yl.

Preferred heterocycles for Z are 1,2-pyrazol-1-yl, 1,2,4-triazol-1-yl, 1,2,3-triazol-2-yl, tetrazol-1-yl and tetrazol-2-yl, most preferably 1,2,4-triazol-1-yl and tetrazol-2-yl.

$R_a$ and $R_b$ are preferably both hydrogen.

The invention also provides a process for the preparation of a compound of formula (I), or a pharmaceutically acceptable salt thereof, which process comprises:

(a) cyclising a compound of formula (II):

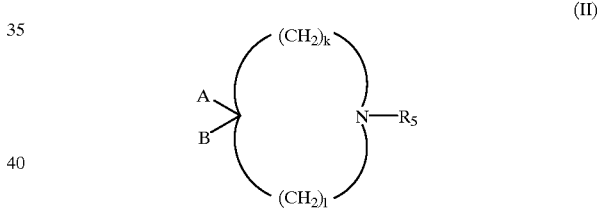

(II)

in which (i) A represents Z or a group convertible thereto and B represents $—(CH_2)_jL_1$ where $L_1$ is a leaving group or A and $L_1$ together represent —COO—; one of j, k and l is 1 and the other two independently represent an integer of 2 or 3, and $R_5$ represents hydrogen or an N-protecting group; to give a compound of formula (IIa):

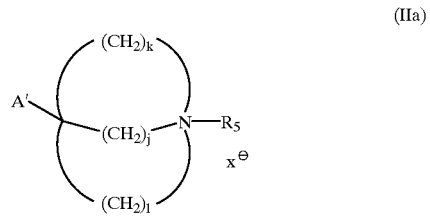

(IIa)

in which A' represents Z or a group convertible thereto, $x^-$ is an anion and the remaining variables are as previously defined;

or (ii) A represents an electron withdrawing group, B represents hydrogen and $R_5$ represents $—(CH_2)_j L_2$ where $L_2$ is a leaving group; one of k and l is 1 and the other and j independently represent an integer of 2 or 3; to give a compound of formula (IIb):

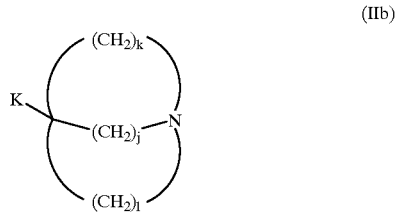

in which K represents an electron withdrawing group or A' and the remaining variables are as previously defined; and thereafter, optionally or as necessary and in any appropriate order, removing any $R_5$ N-protecting group, converting K to A', converting A' to Z, optionally interconverting Z and/or forming a pharmaceutically acceptable salt; or (b) cyclising a compound of formula (III):

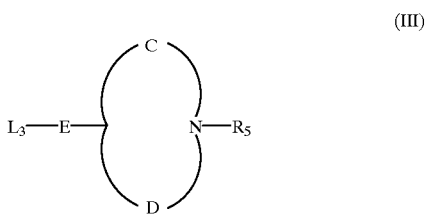

where $R_5$ is hydrogen or an N-protecting group, and either C is one, D is another and E is the remainder of $-(CH_2)_r-$, $-(CH_2)_s-$ and $-(CH_2)_t-CR_aA'-CHR_b-$ or groups convertible thereto, A' is Z or a group convertible thereto and $L_3$ is a leaving group; or C is one and E is the other of $-(CH_2)_r-$ and $-(CH_2)_s-$ or groups convertible thereto and D represents $-(CH_2)_t-CR_aA'-CHR_b-$ where A' and $L_3$ together represent $-COO-$, and thereafter, optionally or as necessary and in any appropriate order, converting C, D and E to $-(CH_2)_r-$, $-(CH_2)_s-$ and $-(CH_2)_t-CHR_aA'-CHR_b-$, removing any $R_5$ protecting group, converting A' to Z, optionally interconverting Z and/or forming a pharmaceutically acceptable salt; or (c) cyclising a compound of formula (IV):

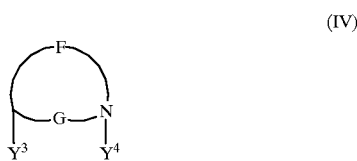

where F is one and G is the other of $-(CH_2)_r-$ and $-(CH_2)_s-$ or groups convertible thereto, and one of $Y^3$ and $Y^4$ is $-(CH_2)_u-K$ and the other is $-(CH_2)_v W$ or $-(CH_2)_v L_4$ where K and W are electron withdrawing groups, $L_4$ is a leaving group, u is 1 or 2 and v is 0 or 1, with the provisos that, when $Y^4$ is $-(CH_2)_v W$, v is 1, and $Y^4$ is not $-(CH_2)_v L_4$, u and v being such that the desired compound of formula (I) is obtained, and thereafter, optionally or as necessary and in any appropriate order, hydrolysing and decarboxylating the cyclisation product and converting the carbonyl group to $CHR_aA'$ where A' is Z or a group convertible thereto, converting K to A' as defined, converting A' to Z, converting F and G to $-(CH_2)_r-$ and $-(CH_2)_s-$ as appropriate, interconverting Z and/or forming a pharmaceutically acceptable salt.

It will be appreciated that the product of process variant (a) is a compound of formula (I) in which variable Y is hydrogen and that the product of process variant (b) or (c) is a compound of formula (I) in which variable X is hydrogen.

In process variant (a), examples of the leaving groups $L_1$ and $L_2$ include halo such as chloro or bromo, tosyloxy and mesyloxy.

Examples of $R_5$ when an N-protecting group include benzyl and substituted benzyl.

Examples of A and A' when other than Z include hydroxy, alkoxycarbonyl, benzyloxycarbonyl and cyano.

The cyclisation reaction is a nucleophilic substitution which may be carried out under conventional conditions appropriate to the groups A and B. Thus, when B is $(CH_2)_j Br$ and A is $C_{1-4}$ alkoxycarbonyl, the cyclisation is carried out in an inert solvent such as toluene or ether at elevated temperature. When B is $(CH_2)_j OTos$ or $(CH_2)_j O\text{-}Mes$, it is preferably obtained by treatment of a $(CH_2)_j OH$ group with a suitable reagent such as tosylchloride or mesyl chloride, in a base such as pyridine, whereupon the cyclisation may proceed at ambient temperature, or at elevated temperature in an inert solvent such as toluene. This route is suitable where A is hydroxy or Z and $R_5$ is preferably an N-protecting group and is the preferred route to compounds of formula (I) where X is Z and (r,s,t) is (2,1,0). When A and $L_1$ together represent $-COO-$, the cyclisation may be carried out in a lower alkanol such as ethanol in the presence of acid such as hydrogen bromide. In the resulting compound of formula (IIa), A' will be an alkoxycarbonyl group corresponding to the lower alkanol used for the cyclisation.

Where $R_5$ is an N-protecting group such as benzyl, this may be removed by conventional hydrogenation, preferably catalytically over a suitable catalyst such as Pd/C. Where A' or K is benzyloxycarbonyl, deesterification and deprotection may be effected simultaneously by conventional hydrogenation.

Examples of K and A when an electron withdrawing group include $C_{1-4}$ alkoxycarbonyl and cyano.

When A is an electron withdrawing group such as $C_{1-4}$ alkoxycarbonyl, B is hydrogen and $R_5$ is $-(CH_2)_j L_2$ where $L_2$ is, for example, chloro, the cyclisation may be effected by treatment of the compound of formula (II) with lithium diisopropylamide.

In process variant (b), examples of leaving groups $L_3$ include halo such as chloro and hydroxy. In the group $-(CH_2)_t-CHR_aA'-CHR_b-$, examples of A' include hydroxy and cyano. Examples of groups convertible to $-(CH_2)_t-CR_aA'-CHR_b-$ include $-(CH_2)_t-COCH_2-$ and $-(CH_2)_t-CHA'-CH_2-$. In process variant (c), examples of $L_4$ include those given for $L_3$. Examples of electron withdrawing groups K and W include $C_{1-4}$ alkoxycarbonyl and cyano. In the group $-(CH_2)_t-CHA'-CH_2-$, examples of A' include hydroxy, cyano and formyl.

In process variant (b), where $L_3$ is hydroxy and D is $-(CH_2)_t-CHOH-CH_2-$, the cyclisation of compounds of formula (III) may be carried out by pyrolysis, by the method of D. O. Spry and H. S. Aaron, J. Org. Chem., 1969, 34, 3674, to yield a compound where A' is hydroxy.

Where E is $-(CH_2)_t-CO-CH_2-$, the cyclisation may be carried out under basic conditions where $R_5$ is benzyl (F. I. Carrol, A. M. Ferguson, and J. B. Lewis, J. Org. Chem. 31, 2957, 1966).

Where $L_3$ and A' together represent —COO—, the cyclisation is a rearrangement reaction which can be carried out under acid conditions in a polar solvent, such as hydrogen bromide in ethanol, at ambient temperature, to yield a compound where A' is a carboxy ester group. It is preferred to protect the nitrogen atom with an $R_5$ N-protecting group such as benzyl, which may be subsequently removed by hydrogenation over a suitable catalyst such as Pd/C.

In process variant (c), where $Y^3$ and $Y^4$ both contain carboxy ester groups the cyclisation of compounds of formula (IV) is a Dieckmann reaction which is catalysed by a base such as potassium t-butoxide at elevated temperature in a solvent such as toluene.

The resulting β-keto ester is hydrolysed and decarboxylated under conventional conditions such as heating at reflux in dilute hydrochloric acid.

In process variant (c) where $Y^3$ and $Y^4$ both contain cyano groups the cyclisation is a Thorpe reaction which is catalysed by a base such as potassium t-butoxide at elevated temperature in a solvent such as toluene.

The resulting β-keto nitrile is hydrolysed and decarboxylated under conventional conditions such as heating at reflux in dilute hydrochloric acid.

Where $Y^3$ is —(CH$_2$)$_v$L$_4$, the cyclisation may be carried out as described in EP-0094742 under basic conditions such as sodium hydride and potassium t-butoxide, in an inert polar solvent such as dimethylformamide.

Conversions of the carbonyl group from process variants (b) and (c) and of groups A' and K, and interconversions of Z, may be carried out conventionally, see for example standard text books on heterocyclic chemistry such as 'Comprehensive Heterocyclic Chemistry', A. R. Katritzky and C. W. Rees, Pergamon, 1984.

The A' or K group is first converted, as necessary, to a suitable starting group Z' for the chosen conversion reaction to give the required group Z. The carbonyl group from process variants (b) and (c) is converted to a group CR$_a$Z' or C=N—NH$_2$.

An A' hydroxy group may be oxidised to a carbonyl group by treatment with chromic acid or using dimethyl sulphoxide and dicyclohexylcarbodiimide.

A carbonyl group may be converted to a C=N—NH$_2$ hydrazone group by successive treatment with N,N-dimethylhydrazine and hydrazine. Reduction of the hydrazone with lithium aluminium hydride affords the hydrazine, a CHZ' group where Z' is hydrazino.

Alternatively, the carbonyl group may be converted to CHZ' where Z' is hydrazino by treatment with t-butyl carbazate followed by reduction to the t-butyloxycarbonyl hydrazine by catalytic hydrogenation and removal of the ester function by acid hydrolysis.

A carbonyl group may be reacted with hydroxylamine hydrochloride to give an oxime which can then be reduced with either lithium aluminium hydride in tetrahydrofuran at elevated temperature or sodium in isoamyl alcohol, depending on the stereochemistry required, to give a Z' amino group.

Alternatively, the carbonyl group may be reduced to a Z' hydroxy group with a suitable reducing agent such as sodium borohydride in ethanol at ambient temperature, or sodium in ethanol at elevated temperature, such as the boiling point of the solvent, under an inert atmosphere such as nitrogen, depending on the stereochemistry required. Hydrogenation in the presence of Adam's catalyst, PtO$_2$, provides a stereospecific, endo product.

A Z' hydroxy group may be converted to azido by first converting it to a good leaving group such as mesyloxy or tosyloxy and then displacing it with azide ion. A Z' azido group may be reduced to a Z' amino group by reduction with hydrogen catalysed by palladium on carbon.

A Z' alkoxycarbonyl group may be obtained by conventional acid hydrolysis of a Z' cyano group, followed by esterification.

A Z' bromo group may be obtained from a Z' alkoxycarbonyl group by conversion of the latter to chlorocarbonyl by hydrolysis and treatment with thionyl chloride. The chlorocarbonyl group is reacted with N-hydroxypyridine-2-thione sodium salt, dimethylaminopyridine and triethylamine in bromotrichloromethane.

A Z' alkoxycarbonyl group may be converted to a Z' amino group by hydrolysis with aqueous acid to a carboxyl group followed by treatment with sodium azide in concentrated sulphuric acid to give an amino group via a Schmidt degradation (ref. organic Reactions Volume 3 Chapter 8 p307–333, 1946, Publ. John Wiley and Son).

A Z' isocyanide group may be obtained from a Z' amino group by formylating with a mixture of formic acid and acetic anhydride and then dehydrating the resulting formamide with phosgene in dichloromethane. Alternatively a Z' isocyanide group may be obtained from a hydrazino group by diazotization to form an azide and then reduction to an amino group and continue as above.

A Z' hydrazino group may be obtained from a Z' amino group by treatment with formaldehyde and potassium cyanide to form a cyanomethylamino group which is then hydrolysed with aqueous hydrochloric acid to afford the amino carboxylic acid. Diazotisation with sodium nitrite in aqueous hydrochloric acid affords the N-nitroso group which can be cyclised to the sydnone with acetic anhydride. The hydrazine can be obtained from this by hydrolysis with aqueous hydrochloric acid (ref. H. U. Daeniker, Helv. Chem. Acta 1967, 50, 2008).

Alternatively, a Z' hydrazino group may be obtained from a Z' hydroxy group by treatment with tosyl chloride in pyridine at ambient temperature to afford a tosylate group. This can be converted to a hydrazino group by treatment with anhydrous hydrazine at elevated temperature, for example at reflux for a number of hours.

Alternatively, a Z' hydrazino group may be obtained from a Z' bromo group by treatment with anhydrous hydrazine, again at reflux for a number of hours.

When Z represents a 3-substituted-1,2-pyrazol-1-yl group, a Z' hydrazino group may be treated with the acetal or bis acetal of $R_1$COCH$_2$CHO, where $R_1$ is hydrogen or an alkyl, alkenyl, alkynyl or cyclopropyl group, under acidic conditions at elevated temperature.

A Z 3- or 5-amino-1,2-pyrazol-1-yl group may be obtained by treatment of a Z' hydrazino group with 2-chloroacrylonitrile under basic conditions at low temperature.

When Z represents a 3-substituted-1,2,4-triazol-1-yl group, a Z' hydrazino group may be treated with the appropriate imidate of the form ROC(=NH)—$R_1$ where $R_1$ is hydrogen or an alkyl, alkenyl, alkynyl or cyclopropyl group and R is a lower alkyl group, under basic conditions followed by treatment of the resulting amidrazone with anhydrous formic acid or triethyl orthoformate. Where $R_1$ is hydrogen the hydrazino group may alternatively be treated with Gold's reagent, (CH$_3$)$_2$N—CH=N—CH=N$^+$(CH$_3$)$_2$Cl$^-$.

Where the hydrazone is used in place of the hydrazine, the product is a compound of formula (I) in which Ra and R$_b$ together represent a bond.

When Z represents an unsubstituted tetrazol-1-yl group a Z' isocyano group may be treated with ammonium azide in methanol for a prolonged period of time.

A Z tetrazol-2-yl group may be obtained by conversion of a hydrazine via literature procedures ref J. A. Bladin, Chem. Ber. 1885, 1544.

A Z 1,2,3-triazol-1-yl group may be obtained by treating a Z' azide group with acetylene dicarboxylic acid followed by heating which causes decarboxylation.

In an alternative strategy, Z is introduced by displacing a Z' leaving group such as methanesulphonyloxy or bromo with a Z⁻ anion generated by preparing the sodium salt of the azole ZH by treatment with sodium in ethanol. The displacement reaction is carried out at elevated temperature in an inert, polar solvent such as dimethylformamide. The displacement results in a reversal of the stereochemistry at the assymetric carbon.

Interconversion of carbon substituents $R_1$ within a group Z may be carried out conventionally. Thus, for 1,2,4-triazoles, an amino group may be converted to halo such as chloro, azide or —NHNH$_2$, via a diazonium intermediate. The diazonium intermediate may be obtained by treatment of the amino group with nitrous acid. A halo group may be obtained by displacement of the diazonium ion with cuprous halide at elevated temperature. An azide group may be obtained by displacement of the diazonium ion with sodium azide. A hydrazine may be obtained by reduction of the diazonium ion. A nitro group may be obtained by displacement of the diazonium ion with nitrite ion at elevated temperature.

Halo substitutents such as bromine, chlorine or iodine may be introduced into the 5 position of 1,2,4-triazoles and into 2-yl tetrazoles by treatment of the unsubstituted azole with base such as t-butyllithium in pentane followed by reaction with halogen source such as bromine, chlorine in carbon tetrachloride or iodine. A chloro substituent may be converted by reaction with a nucleophile such as methoxide; and alkoxycarbonyl groups may be converted, via carboxy, to an amino substituent.

A cyano group may be introduced into 2-yl tetrazoles by conversion of hydrogen to formyl by treatment with t-butyl lithium followed by N-methyl formanilide. The formyl group is converted to an aldoxime by treatment with hydroxylamine hydrochloride. The aldoxime may then be dehydrated with a suitable dehydrating agent such as acetic anhydride to afford the required cyano group.

Where applicable, an endo isomer may be obtained by epimerisation of a corresponding exo isomer, the epimerisation reaction being effected by standard procedures at any convenient stage in the process but preferably before the introduction of the group Y.

In a further aspect the invention provides a process for the preparation of a compound of formula (I), or a pharmaceutically acceptable salt thereof, which process comprises reacting a compound of formula (IVa):

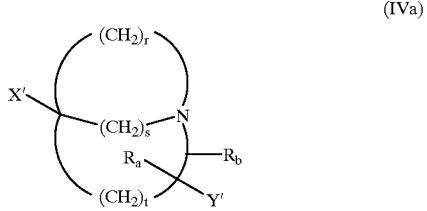

(IVa)

in which $R_a$, $R_b$, r,s and t are as defined in formula (I), one of X' and Y' represents hydrogen and the other represents Z' wherein Z' is a group convertible to Z as defined in formula (I), to convert Z' to Z and thereafter optionally forming a pharmaceutically acceptable salt.

Intermediates of formula (IVb) and salts thereof:

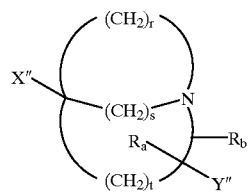

(IVb)

in which $R_a$, $R_b$, r,s, and t are as defined in claim 1, one of X" and Y" represents hydrogen and the other represents Z" where Z" is hydrazino, azido or isocyano or $R_a$ and Z" together are a hydrazone group are novel and form part of the invention.

Compounds of formula (II) may be prepared conventionally, for example as described in EP-0287356.

Where A is $C_{1-4}$ alkoxycarbonyl, B is $(CH_2)_j L1$ and $R_5$ is hydrogen or an N-protecting group, the compound of formula (II) may be prepared by treating a compound of formula (V):

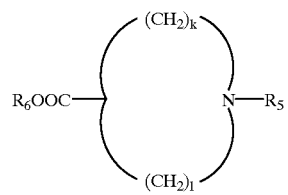

(V)

where $R_6$ is $C_{1-4}$ alkyl and the remaining variables are as previously defined, with lithium diisopropylamide, prepared in situ from diisopropylamine and n-butyllithium followed by reaction with a compound $L_5(CH_2)_j L_1$ where $L_5$ is a leaving group, in an inert solvent such as ether at depressed to elevated temperature. Both $L_1$ and $L_5$ are suitably bromo.

Where A is Z such as optionally substituted 1,2,4-triazol-1-yl, B is $CH_2L_1$, k and l are each 2 and $R_5$ is an N-protecting group, the compound of formula (II) may be prepared by treating a compound of formula (V) defined above with lithium diisopropylamide prepared as aforesaid followed by reaction with di-t-butylazadicarboxylate at depressed to ambient temperature. The resulting protected 4-hydrazino group is deprotected conventionally by acid hydrolysis and the free hydrazino group converted to an optionally substituted 1,2,4-triazol-1-yl group as described earlier. Other Z groups may be obtained analogously. The $R_6OOC$— group also in the 4 position is then converted to —CH$_2$OH by reduction with lithium aluminium hydride and the OH converted to other $L_1$ as described earlier.

Where A and $L_1$ together represent —COO— and j is 2, the compound of formula (II) may be prepared by reacting the compound of formula (V), treated with lithium diisopropylamide as before, with ethylene oxide in an inert solvent such as ether at depressed to elevated temperature.

Alternatively, the compound of formula (II) where A and $L_1$ together represent —COO, j is 2, k is 2 and l is 1 may be prepared by a 1,3-dipolar cycloaddition reaction which involves reacting a compound of formula (VI):

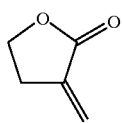

(VI)

with a compound of formula (VII):

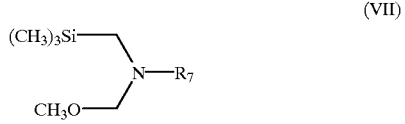

(VII)

where $R_7$ is an N-protecting group, in the presence of a catalytic amount of trifluoroacetic acid.

Where A is an electron withdrawing group such as $C_{1-4}$ alkoxycarbonyl, B is hydrogen and $R_5$ is $(CH_2)_jL_2$, the compound of formula (II) may be prepared by reacting the compound of formula (V) where $R_5$ is hydrogen with a compound $L_5(CH_2)_jL_2$ where $L_5$ is as previously defined, in a solvent such as acetone in the presence of a base such as potassium carbonate. The leaving group $L_5$ is preferably bromo and $L_2$ is preferably chloro.

Compounds of formulae (V) are known compounds or may be prepared by analogous methods to those for preparing known compounds. The compound of formula (V) where k is 2, l is 1 and $R_5$ is benzyl may be prepared by the cyclisation of di-$C_{1-4}$ alkyl itaconate in the appropriate alkanol with benzylamine at elevated temperature, followed by reduction of the resulting oxo group at the 2-position of the pyrrolidine ring with $BH_3$ in tetrahydrofuran, at ambient to elevated temperature.

Alternatively, and preferably, a dipolar cycloaddition of a $C_{1-4}$ alkyl acrylate with a compound of formula (VII) in the presence of a catalytic amount of trifluoroacetic acid yields a compound of formula (V) directly.

Intermediates of formulae (III) and (IV) are known compounds (e.g. as described in EP-A-0094742 or EP-A-0261763) or may be prepared analogously.

Intermediates of formula (III) where A' and $L_3$ together represent —COO— are described in, for example, Kuthan et al., Coll. Czechoslov. Chem. Comm., 1977, 42, 283 or may be prepared therefrom by conventional hydrogenation of the pyridine ring over 5% Pt/C, and benzylation of the nitrogen atom by treatment with benzyl bromide and potassium carbonate in dry acetone.

The compound of formula (III) where A' and $L_3$ together represent —COO—, t=0, C is —$CH_2$— and E is —$(CH_2)_2$— may be prepared by a 1,3-dipolar cycloaddition reaction of a compound of formula (VII) with 5,6-dihydro-2H-pyran-2-one in the presence of a catalytic amount of trifluoroacetic acid.

Intermediates of formula (III) where $L_3$ is a leaving group are described in, for example, Spry et al., J. Org. Chem., 1969, 34, 3674 and Hasse et al., Chem. Ber., 1960, 93, 1686.

Intermediates of formula (IV) are described in or may be prepared from intermediates of formula (V) as described in, for example, Martell et al., J. Pharm. Sci., 1963, 52(4), 331, Sternbach et al., J. A. C. S., 1952, 74, 2215, Thill et al., J. Org. Chem., 1968, 33, 4376 and EP-0 094 742.

Compounds of formulae (VI) and (VII) may be prepared conventionally. Thus, a compound of formula (VI) may be obtained by the reaction of γ-butyrolactone with ethyl formate in the presence of base such as sodium hydride followed by reaction of the resulting formyl derivative (as the enol salt) with formaldehyde. A compound of formula (VII) may be obtained by the reaction of the primary amine $R_7NH_2$ successively with chloromethyltrimethylsilane and formaldehyde followed by methanol and anhydrous potassium carbonate.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing.

Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50 mg; and such unit doses may be administered more than once a day, for example two or three times a day, so that the total daily dosage is in the range of about 0.01 to 5 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

DESCRIPTION 1

3-Quinuclidinyl-hydrazone (D1)

3-Quinuclidinone (10 g, 0.08 mol) was dissolved in dry EtOH (20 ml) and N,N-dimethylhydrazine (16 ml, 0.21 mol) was added. The yellow solution was heated at reflux overnight, and then evaporated to dryness under reduced pressure. The yellow syrup (12.34 g, 92%) crystallised on standing to afford N-(3-quinuclidinyl)-N'N'-dimethyl hydrazone. This compound (0.62 g, 3.7 mmol) was then dissolved in dry EtOH and anhydrous hydrazine (0.8 ml, 25 mmol) added. The solution was heated at reflux for 4.5 h, and then evaporated to dryness under reduced pressure. The resulting white solid was purified by Kugelrohr distillation (b.p. 170° C., 0.2 mmHg) to afford the title compound as a white crystalline solid (0.48 g, 93%). m.p. 93–95° C.

$^1$H nmr (CDCl$_3$, 270 MHz); 1.80 (4H, m), 2.40 (1H, pentet), 2.88 (4H, m), 3.48 (2H, s), 4.78 (2H, bs, NH$_2$). MS: C$_7$H$_{13}$N$_3$: M$^+$ 139

DESCRIPTION 2

(±) 3-Quinuclidinyl-hydrazine (D2)

3-Quinuclidinyl-hydrazone (D1) (1.09 g, 7.84 mmol) was dissolved in dry THF (20 ml) and the solution added dropwise to an iced suspension of LiAlH$_4$ (600 mg, 15.8 mmol) in THF (5 ml) under N$_2$, and the solution allowed to warm to room temperature. This was then heated at reflux under N$_2$ for 24 h. The reaction was quenched with water (0.6 ml), 10% NaOH (1.8 ml) and water (0.6 ml), and the white precipitate filtered off and washed with dry ether. The filtrate was evaporated to dryness under reduced pressure to yield a clear colourless oil (1.0 g, 90%), which was used directly in the next stage.

$^1$H nmr (CDCl$_3$, 270 MHz); 1.54 (2H, bm), 1.80 (2H, bm), 2.36 (1H, m), 2.53 (1H, m), 2.80 (4H, bm), 3.18 (2H, m).

DESCRIPTION 3

1-$^t$Butyloxycarbonyl-2-(3-quinuclidinyl)-hydrazone (D3)

3-Quinuclidinone (1.25 g, 10 mmol) was dissolved in 60–80 petroleum ether (50 ml) and $^t$butyl carbazate (2.0 g, 15 mmol) was added. The solution was heated at reflux for 24 h, allowed to cool overnight, and the resulting crystals filtered to yield the title compound as a white crystalline solid (2.301 g, 96%), m.p. 170–172° C.

$^1$H nmr (CDCl$_3$, 250 MHz); 1.51 (9H, S, $^t$Bu), 1.86 (4H, m), 2.83 (5H, complex m), 3.45 (1.65H, s) with 3.55 (0.35H, s). $^{13}$C nmr (CDCl$_3$, 67 MHz); 26.5 (CH$_2$), 28.2 ($^t$Butyl), 31.0 (CH), 47.3 (CH$_2$), 52.7 (CH$_2$), 81.1 ($^t$Bu—C), 152.9 (C=N), 159.9 (C=O). MS: C$_{12}$H$_{21}$N$_3$O$_2$ requires 239.1632; observed 239.1634; Analysis: C$_{12}$H$_{21}$N$_3$O$_2$; % required: C, 60.23; H, 8.85; N, 17.56; % found: C, 59.83; H, 8.77; N, 17.46

DESCRIPTION 4

(±) 1-$^t$Butyloxycarbonyl-2-(3-quinuclidinyl) hydrazine (D4)

1-$^t$Butyloxycarbonyl-2-(3-quinuclidinyl)-hydrazone (D3) (1.0 g, 4.18 mmol) was dissolved in ethanol (100 ml) and a solution of anhydrous oxalic acid (0.370 g, 4.0 mmol) in ethanol (20 ml) was added. Palladium on charcoal (10% 0.3 g) was added under nitrogen and the solution hydrogenated at atmospheric pressure and 35° C. for 24 h. The mixture was filtered through celite under nitrogen, the filtrate evaporated to dryness under reduced pressure, and the residue dissolved in saturated aqueous potassium carbonate. The aqueous solution was extracted with ethyl acetate (2×250 ml), the organic solutions dried (Na$_2$SO$_4$), filtered and evaporated to dryness under reduced pressure to yield the title compound (D4) as a clear colourless oil (1.01 g, 100%) which crystallised on standing.

$^1$H nmr (CDCl$_3$, 270 MHz); 1.47 (9H, s, $^t$Bu), 1.64 (1H, m), 1.86 (2H, m), 2.42 (1H, dm), 2.78 (5H, complex m), 3.66 (3H, m). $^{13}$C nmr (CDCl$_3$, 67 MHz); 20.0 (CH$_2$), 24.1 (CH), 25.4 (CH$_2$), 28.4 ($^t$Bu—Me), 47.0 (CH$_2$), 47.5 (CH$_2$), 53.4 (CH$_2$), 56.1 (CH), 80.5 ($^t$Bu—C), 156.9 (C=O). MS: C$_{12}$H$_{23}$N$_3$O$_2$ requires 241.1784; observed 241.1792

DESCRIPTION 5

(±) 3-Quinuclidinyl-hydrazine dihydrochloride (D5)

1-$^t$Butyloxycarbonyl-2-(3-quinuclidinyl)-hydrazine (D4) (1.0 g, 4.2 mmol) was dissolved in 10% HCl/MeOH (40 ml) and heated at reflux for 30 min. The solution was evaporated to dryness under reduced pressure, and recrystallised from MeOH and diethyl ether, to afford the title compound as a white crystalline solid (0.78 g, 87%), m.p. 245–250° C., decomp.

¹H nmr (d₆ DMSO, 270 MHz); 1.87 (2H, m), 2.05 (1H, m), 2.28 (1H, m), 2.50 (1H, m), 3.09 (1H, d), 3.31 (4H, bm), 3.62 (2H, m). ¹³C nmr (d₆ DMSO, 67 MHz); 16.5 ($CH_2$), 21.0 ($CH_2$), 21.9 (CH), 44.7 ($CH_2$), 45.5 ($CH_2$), 49.9 ($CH_2$), 52.2 (CH). MS: $C_7H_{15}N_3$ requires 141.1272; observed 141.1265

DESCRIPTION 6

(±) 1-ᵗButloxycarbonyl-2-[3-(1-azabicyclo[2.2.1]-heptanyl)]-hydrazone (D6)

3-Oxo-1-azabicyclo[2.2.1]heptane[1] (4.2 g, 0.038 mol) was dissolved in petroleum ether (60–80°) (250 ml) and diethyl ether (10 ml). ᵗButyl carbazate (10 g, 0.0758 mol) was added and the solution heated at reflux for 24 h, allowed to cool overnight, and then evaporated to dryness under reduced pressure to yield a yellow oil, containing both syn and anti isomers of the product (D6) and excess ᵗbutyl carbazate. The oil was used directly in the next step.

¹H NMR ($CDCl_3$, 270 MHz); 1.68 (1H, m), 1.92 (1H, A), 2.58 (1H, dt), 2.73 (1H, bq), 2.99–3.50 (4H, complex m). ¹³C NMR ($CDCl_3$, 67 MHz); 27.4 and 28.3 (ᵗBu-Me), 38.5, 44.3, 52.9 and 53.3, 57.0, 60.7 and 61.2, 81.3 (ᵗBu-quat-C), 152.9 (C=N), 162.9 (C=O). MS: $C_{11}H_{19}N_3O_2$ requires 225.1487; observed 225.1474

[1] D. O. Spry and H. S. Aaron, *J. Org. Chem.*, 1969, 34, 3674.

DESCRIPTION 7

(±) exo and endo (1-Azabicyclo[2.2.1]heptan-3-yl) hydrazine dihydrochloride (D7)

The mixture of 1-ᵗbutyloxycarbonyl-2-[3-(1-azabicyclo[2.2.1]heptanyl)]hydrazone (D6) and unreacted ᵗbutylcarbazate was dissolved in ethanol (300 ml) and excess anhydrous oxalic acid (4 g) added. Palladium on charcoal (10% 0.5 g) was added under $N_2$ and the mixture was hydrogenated at atmospheric pressure and 45° C. for 6 h. The solution was then filtered through celite, evaporated to dryness under reduced pressure, dissolved in saturated aqueous $K_2CO_3$ and extracted with EtOAc (4×500 ml). The organic extracts were dried ($Na_2SO_4$), filtered and evaporated to dryness to yield a yellow oil which was purified by column chromatography (basic alumina, eluting with EtOAc/2% MeOH) to yield the saturated ᵗbutyloxycarbonyl hydrazine as a mixture of exo and endo isomers [7.10 g, 83% based on the starting ketone in Description 6]. This compound (6.77 g, 0.030 mol) was dissolved in MeOH/HCl (250 ml) and heated at reflux for 20 min. The mixture was evaporated to dryness under reduced pressure and recrystallised from methanol/diethyl ether to yield the title compound as a white crystalline solid (4.34 g, 72%), m.p. 245–246° C. (decomp.).

¹H NMR (d₆ DMSO, 270 MHz); 1.46 and 1.79 together (1H, m), 2.01 (1H, complex M), 2.75–3.85 (8H, complex bm). ¹³C NMR (d₆ DMSO, 67 MHz); 19.8 ($CH_2$), 23.6 ($CH_2$), 50.9 and 51.7 ($CH_2$), 55.4 and 55.6 ($CH_2$), 56.1 and 56.4 (CH), 57.9 and 58.9 (CH).

DESCRIPTION 8

(±) 3-Methanesulphonyloxy-1-azabicyclo[2.2.2]octane (D8)

Quinuclidin-3-ol (10.0 g, 0.0787 mol) was dissolved under $N_2$ in dry dichloromethane (200 ml) and cooled in an ice bath to 0° C. Methanesulphonyl chloride (7.3 ml, 10.8 g, 0.094 mol, 1.2 eq) and dry pyridine (7.64 ml, 7.46 g, 0.094 mol, 1.2 eq) were added and the mixture stirred at 0° C. for 20 min. The solution was then warmed to r.t. and stirred under $N_2$ for 1 h. Saturated aqueous potassium carbonate solution (150 ml) was added, and the organic layer extracted and collected. The aqueous layer was re-extracted with EtOAc (3×200 ml), the organic solutions dried ($Na_2SO_4$), filtered, and evaporated to dryness under reduced pressure to yield a pale yellow oil which was pumped under high vacuum to remove any last traces of pyridine to yield the title compound (D8) (15.8 g, 98%).

¹H NMR ($CDCl_3$, 270 MHz); 1.67 (4H, m), 2.18 (1H, pentet), 2.85 (5H, bm), 3.03 (3H, s, $SO_2Me$), 3.38 (1H, q), 4.82 (1H, m, CHOMs).

DESCRIPTION 9 endo-1-Azabicyclo[2.2.1]heptan-3-ol (D9)

1-Azabicyclo[2.2.1]heptan-3-one* (6.2 g, 0.056 mol) was dissolved in EtOH (50 ml). $PtO_2$ (Adam's catalyst) (1 g) was added under nitrogen and the mixture hydrogenated at atmospheric pressure and 45° C. for 6 h. The suspension was filtered under nitrogen through celite, the solid washed with EtOH, and the filtrate evaporated to dryness under reduced pressure and pumped dry under high vacuum to yield the title compound (D9) as a beige solid (6.2 g, quantitative)

¹H NMR ($CDCl_3$, 270 MHz); 1.43 (1H, m), 2.05 (2H, m), 2.42 (1H, dd), 2.63 (3H, bm), 2.90 (1H, m), 3.05 (1H, m), 4.38 (1H, m, CHOH).

*D. O. Spry and H. S. Aaron, *J. Org. Chem.*, 1969, 34, 3674.

DESCRIPTION 10 endo-3-Methanesulphonyloxy-1-azabicyclo[2.2.1] heptane (D10)

endo-1-Azabicyclo[2.2.1]heptan-3-ol (D9) (0.58 g, 5.13 mmol) was dissolved in dry dichloromethane (25 ml), the solution cooled on ice to 0° C., and methanesulphonyl chloride (0.48 ml, 1.2 eq) with dry triethylamine (0.86 ml, 1.2 eq) were added. The mixture was allowed to warm to room temperature and stirred for 2 h. The solution was washed with an equal volume of saturated aqeuous potassium carbonate solution, and the aqueous layer was extracted with EtOAc (3×100 ml). The organic solutions were dried ($Na_2SO_4$), filtered and evaporated to dryness under reduced pressure to yield an orange oil. This was purified by column chromatography (basic alumina, eluting with EtOAc/1–3% MeOH) to yield the title compound (D10) as a pale yellow oil (0.70 g, 71%).

¹H NMR ($CDCl_3$, 270 MHz); 1.57 (1H, m), 1.92 (1H, m), 2.47 (2H, complex m), 2.67 (2H, m), 2.92 (2H, m), 3.02 (3H, s, $SO_2Me$), 3.20 (1H, m), 5.08 (1H, m, CHOMS).

DESCRIPTION 11 endo-1-Azabicyclo[3.2.1]octan-3-ol (D11)

1-Azabicyclo[3.2.1]octan-3-one* (6.0 g, 0.048 mol) was dissolved in EtOH (100 ml) and platinum oxide (Adam's catalyst) (1.0 g) added under nitrogen. The suspension was hydrogenated at atmospheric pressure and 40° C. for 7 h, and then filtered under nitrogen through celite.

The solid was washed with EtOH, and the filtrate was evaporated to dryness under reduced pressure to yield the title compound (D11) as a white solid (6.0 g, quantitative).

¹H NMR ($CDCl_3$, 270 MHz); 1.70 (2H, m), 1.93 (1H, dm), 2.14 (2H, m), 2.53 (2H, m), 2.91 (3H, complex m), 3.32 (1H, m), 3.68 (1H, m), 3.79 (1H, bs, OH). *D. P. Thill and H. S. Aaron, *J. Org. Chem.*, 1968, 33, 4376.

DESCRIPTION 12 endo-3-Methanesulphonyloxy-1-azabicyclo[3.2.1]octane (D12)

endo-1-Azabicyclo[3.2.1]octan-3-ol (D11) (2.0 g, 0.0158 mol) was dissolved in dichloromethane (50 ml) and the solution cooled on ice to 0° C. Methanesulphonyl chloride (1.46 ml, 1.2 eq) and pyridine (1.57 ml, 1.2 eq) were added with stirring, the mixture allowed to warm to room temperature and stirred for 1.5 h. The organic solution was then washed with an equal volume of aqueous saturated potassium carbonate solution and the aqueous layer extracted with EtOAc (3×100 ml). The organic extracts were dried ($Na_2SO_4$), filtered and evaporated to dryness under reduced pressure to yield a yellow oil. This was purified by column chromatography, using basic alumina and eluting with EtOAc/MeOH 1–5%, to yield the title compound (D12) as a colourless oil (1.20 g, 37%).

$^1$H NMR ($CDCl_3$, 270 MHz); 1.74 (1H, m), 2.08 (3H, m), 2.21 (1H, m), 2.58 (1H, d), 2.70 (1H, dt), 2.87 (1H, m), 2.94 (3H, s, $SO_2Me$), 3.21 (3H, m), 4.63 (1H, m).

DESCRIPTION 13

5-Methyltetrazole (D13)

Acetonitrile (4.1 g, 5.22 ml, 0.10 mol), sodium azide (7.48 g, 0.115 mol), acetic acid (6.59 ml, 0.115 mol) and isopropanol (20 ml) were mixed and heated in a PTFE-lined autoclave at 130° C. for 5 days, with stirring. The reaction was allowed to cool, transferred to a round-bottomed flask with EtOH, and evaporated to dryness under reduced pressure. The solid was extracted repeatedly with boiling n-butyl acetate, until no further solid dissolved. The organic extracts were evaporated to a small volume under reduced pressure and the solid allowed to crystallise out, to give the title compound (D13) as a pale cream solid (3.25 g, 39%).

$^1$H NMR ($CDCl_3$, 270 MHz); 1.85 (3H, s, Me), 4.12 (1H, bs, NH); M.S. found 84.0436; $C_2H_4N_4$ requires 84.0436.

DESCRIPTION 14

5-Ethyltetrazole (D14)

As for Description 13 using propionitrile (7.13 ml, 0.10 mol) instead of acetonitrile, at 140° C. for 5 days, giving the product (D14) as a pale cream solid (800 mg, 8%)

$^1$H NMR ($d_6$ DMSO, 270 MHz); 1.27 (3H, t, $CH_3$), 2.67 (2H, q, $CH_2$), 4.62 (1H, bs, NH)

General Method for the Synthesis of Azole Sodium Salt (D15–21)

Sodium metal (0.01 mol) was dissolved in EtOH (50 ml) under nitrogen at 5° C., the solution warmed to room temperature and the azole (0.01 mol) added. The suspension was stirred until dissolution occurred, and the solution was then evaporated to dryness under reduced pressure and the white solid dried in a vacuum oven, at 50° C. under high vacuum. The salt was then used directly in the next stage. Salts Made Thus:
(D15) 5-Aminotetrazole**
(D16) 1H-Tetrazole**
(D17) 5-Methyltetrazole (from D13)
(D18) 5-Ethyltetrazole (from D14)
(D19) 1,2,4-triazole**
(D20) 3-Amino-1,2,4-triazole**
(D21) 4-Methyl-1,2,3-triazole*

*Starting material—M. Begtrup, *J. Chem. Soc. Perkin* II, 1976, 736
** Starting material commercially available

DESCRIPTION 22 exo-3-Methanesulphonyloxy-1-azabicyclo[2.2.1]heptane (D22)

exo-1-Azabicyclo[2.2.1]heptan-3-ol* (400 mg, 3.54 mmol) was dissolved in dry dichloromethane (50 ml), the solution cooled on ice to 0° C., and methanesulphonyl chloride (0.27 ml, 1.2 equiv) with dry triethylamine (0.592 ml, 1.2 equiv) were added. The mixture was allowed to warm to room temperature and stirred for 2 h. The organic solution was washed with an equal volume of saturated aqueous potassium carbonate solution, and the aqueous layer extracted with EtOAc (2×100 ml). The organic solutions were dried ($Na_2SO_4$), filtered and evaporated to dryness under reduced pressure to yield a yellow oil which was purified by column chromatography (basic alumina, 1–2% MeOH/EtOAc) to afford the title compound as a clear oil (540 mg, 80%).

$^1$H NMR ($CDCl_3$); 1.11 (1H, m), 1.73 (1H, m), 2.43 (3H, m), 2.77 (2H, dm), 2.87 (1H, d), 2.94 (1H, dm), 3.03 (3H, s, $SO_2Me$), 4.53 (1H, m, CH-OMS)

*Douglas O. Spry and Herbert S. Aaron, *J. Org. Chem.*, 1969, 34, 3674.

DESCRIPTION 23

(±) 5-Bromo-1-azabicyclo[3.2.1]octane (D23)

(±) Ethyl-1-azabicyclo[3.2.1]oct-5-ylcarboxylate (EP 0287356, Example 7, 18.97 g, 0.104 mole) in hydrochloric acid (8N, 200 ml) was heated under reflux for 3 h. The solution was then concentrated in vacuo to a hygroscopic solid which was dissolved in thionyl chloride (150 ml) and heated under reflux for 0.5 h. The mixture was then concentrated in vacuo to give the acid chloride hydrochloride salt as a solid, which was freed from excess thionyl chloride by co-evaporation with toluene. This solid was added in portions to a mixture of the sodium salt of 1-hydroxypyridine-2-thione (17.35 g, 0.116 mole), triethylamine (29 ml, 0.208 mole) and 4-dimethylaminopyridine (0.5 g, 0.004 mole) in dry acetonitrile (300 ml) at −20° C. The mixture was allowed to warm slowly to room temperature then refluxed for 2 h and evaporated in vacuo. Bromotrichloromethane (250 ml) was then added to the residue and the resulting solution was refluxed for 3 h. After cooling the reaction mixture was poured into saturated aqueous potassium carbonate solution (150 ml) and the mixture was extracted with chloroform (4×200 ml). The combined organic extracts were dried ($Na_2SO_4$) and evaporated to give an oil which was subjected to column chromatography on silica using 3–7% methanol/chloroform as eluant to give the crude product which was distilled in vacuo to afford the title compound (D23) as a colourless oil (9.18 g, 47%) b.p. 140° C. at 1.5 mmHg.

$^1$H NMR ($CDCl_3$) δ: 1.57 (1H, m), 1.88 (1H, m), 2.16–2.37 (4H, m), 2.71–2.92 (3H, m), 3.07 (2H, s), 3.18 (1H, m). $^{13}$C NMR ($CDCl_3$) δ: 23.83, 40.73, 42.99, 52.01, 53.86, 62.45, 68.43

DESCRIPTION 24

(±) 1-Azabicyclo[3.2.1]oct-5-ylhydrazine (D24)

(±) 5-Bromo-1-azabicyclo[3.2.1]octane (D23, 1 g, 5.3 mmol) in anhydrous hydrazine (10 ml) was heated at reflux for 0.5 h. The mixture was then cooled and evaporated in vacuo. The residue was taken up in methanol and an aqueous solution of sodium hydroxide (2.63 ml of a 2M solution, 5.3 mmol) was added. The resulting solution was evaporated to dryness then taken up in dry methanol (30 ml) and evaporated to dryness once more. This procedure was repeated once more to remove the last traces of water to give a gum (1.34 g) which was essentially the title compound (D24) and sodium bromide and was used without further purification.
$^{13}$C NMR (d$_6$DMSO) δ: 17.56, 29.30, 32.47, 49.64, 51.97, 58.41, 63.59

DESCRIPTION 25

(±) 3-Azido-1-azabicyclo[2.2.2]octane oxalate salt (D25)

3-Methanesulphonyloxy-1-azabicyclo[2.2.2]octane (D8) (16 g) in dry dimethyl formamide (100 ml) was treated with sodium azide (10.4 g) (0.16 mole, 2 eq) at reflux for 5 h. The reaction was then cooled and concentrated in vacuo. The residue was then partitioned between saturated aqueous potassium carbonate solution and ether. The organic phase was separated and concentrated to a gum. This was chromatographed on alumina in a gradient of 5–10% methanol in ethyl acetate. The main fraction which eluted first was concentrated to a gum which was Kugelrohr distilled to afford a colourless oil (B.P. 90–100° C. at 0.1 mm). The oxalate salt of this oil crystallised from acetone/ether to give the title compound (D25) (4.2 g, 0.0173 mole 22%) m.p. 100–102° C.

$^1$H NMR (CDCl$_3$, 250 MHz) δ: 1.8–2.23 (4H, m), 2.28–2.38 (1H, m), 3.05–3.15 (1H, m), 3.15–3.38 (4H, m), 3.55–3.70 (1H, m), 4.20–4.30 (1H, m).

DESCRIPTION 26

Ethyl 1-benzyl-4-(N,N'-di-tert-butyloxycarbonylhydrazino)piperidin-4-ylcarboxylate (D26)

A solution of diisopropylamine (8.8 ml, 0.063 mol) in ether (400 ml) at −70° C. under nitrogen was treated with 1.6M n-butyllithium in hexane (37.5 ml, 0.060 mol) and stirred for 10 minutes. A solution of ethyl 1-benzylpiperidin-4-ylcarboxylate (13.6 g, 0.055 mol) in ether (70 ml) was added over 5 minutes and the resulting mixture then stirred at −70° C. for 40 minutes, before adding a solution of di-tert-butylazodicarboxylate (13.5 g, 0.058 mol) in ether (80 ml). The reaction mixture was allowed to warm to room temperature over 0.5 h, then stirred for a further 2 h before adding dilute potassium carbonate solution (150 ml). The ether layer was separated, dried (Na$_2$SO$_4$) and concentrated in vacuo to leave an orange oil. This was chromatographed on silica gel eluting initially with 20% ether/60–80 petrol, then with neat ether to afford the title compound (D26) (14.2 g, 54%) as a yellow oil.

$^1$H NMR (CDCl$_3$, 250 MHz) δ: 1.24 (3H, t, J=7 Hz), 1.38–1.62 (18H, m), 1.85–1.97 (1H, m), 2.02–2.15 (1H, m), 2.34–2.55 (4H, m), 2.61–2.75 (2H, m), 3.50 (2H, S), 4.07–4.25 (2H, m), 6.02 and 6.30 (together 1H, each br.s), 7.20–7.35 (5H, m).

DESCRIPTION 27

Ethyl 1-benzyl-4-hydrazinopiperidin-4-yl-carboxylate dihydrochloride salt (D27)

A solution of ethyl 1-benzyl-4-(N,N'-di-tert-butyloxycarbonylhydrazino)piperidin-4-yl-carboxylate (D26, 14.2 g, 0.030 mol) in methanol (50 ml) was treated with 10% HCl/methanol (100 ml) and heated under reflux for 2 h. The solution was concentrated in vacuo and the residue treated with dry toluene (80 ml) and again concentrated in vacuo to remove any traces of moisture. The residue was triturated with ether and the material filtered off and immediately placed in a vacuum dessicator to give the title compound (D27) (9.48 g, 90%) as a very hygroscopic orange solid.

$^1$H NMR (CD$_3$OD, 250 MHz) δ: 1.31 (3H, t, J=7 Hz), 2.05–2.20 (2H, m), 2.38–2.58 (2H, m), 3.25–3.60 (4H, m), 4.29 (2H, q, J=7 Hz), 4.35–4.45 (2H, m), 7.43–7.66 (5H, m).

DESCRIPTION 28

Ethyl 1-benzyl-4-(1,2,4-triazol-1-yl)-piperidin-4-yl carboxylate (D28)

A stirred suspension of ethyl 1-benzyl-4-hydrazinopiperdin-4-ylcarboxylate dihydrochloride salt (D27, 2.0 g, 0.0057 mol) in absolute chloroform (200 ml) was treated with Gold's reagent ([3-(dimethylamino)-2-azaprop-2-en-1-ylidene]-dimethylammonium chloride) (930 mg, 0.0057 mol) and triethylamine (1.6 ml, 0.0114 mol) and the mixture heated at reflux under nitrogen for 2.5 h. The solution was allowed to cool, treated with concentrated potassium carbonate solution and the organic layer separated, dried (Na$_2$SO$_4$) and concentrated in vacuo to leave an orange oil. This was chromatographed on silica gel eluting first with ethyl acetate to obtain the title compound (D28), then with methanol to obtain a high polar intermediate, which on heating under reflux in toluene for 20 minutes gave a further batch of the triazole product. These two batches were combined to give the title compound (D28) (770 mg, 43%) as an orange oil.

$^1$H NMR (CDCl$_3$, 250 MHz) δ: 1.20 (3H, t, J=7 Hz), 2.20–2.75 (8H, m), 3.46 (2H, s), 4.17 (2H, q, J=7 Hz), 7.22–7.38 (5H, m), 7.99 (1H, s), 8.26 (1H, s).

DESCRIPTION 29

1-Benzyl-4-hydroxymethyl-4-(1,2,4-triazol-1-yl) piperidine (D29)

A solution of ethyl 1-benzyl-4-(1,2,4-triazol-1-yl)-piperidin-4-ylcarboxylate (D28, 460 mg, 0.00147 mol) in ether (15 ml) was added dropwise to a stirred suspension of lithium aluminium hydride (67 mg, 0.00175 mol) in ether (25 ml) and dry THF (8 ml) at 0° C. under nitrogen. The reaction mixture was allowed to warm to 15° C. over 20 minutes, then treated with water (0.06 ml), followed by 10% sodium hydroxide solution (0.18 ml) and then water (0.06 ml). The grey precipitate was removed by filtration through a pad of Kieselguhr and the filtrate dried (Na$_2$SO$_4$) and concentrated in vacuo to leave a yellow oil. This was purified by passage through a short silica gel column eluting with 10% methanol/ethyl acetate to give the title compound (D29) (320 mg, 80%) as a pale yellow oil.

$^1$H NMR (CDCl$_3$, 250 MHz) δ: 1.97–2.28 (4H, m), 2.33–2.50 (2H, m), 2.60–2.75 (2H, m), 3.44 (2H, S), 3.70 (2H, S), 4.45 (1H, br.s, OH), 7.22–7.40 (5H, m), 7.77 (1H, s), 8.10 (1H, S).

DESCRIPTION 30

Ethyl 1-benzyl-4-(3-methyl-1,2,4-triazol-1-yl)-piperidin-4-ylcarboxylate (D30)

A solution of ethyl 1-benzyl-4-hydrazino-piperidin-4-ylcarboxylate dihydrochloride salt (D27, 3.0 g, 0.0086 mol)

in methanol (100 ml) under nitrogen was treated with methyl acetimidate hydrochloride (940 mg, 0.0086 mol) and triethylamine (3.7 ml, 0.026 mol) and stirred at room temperature for 3 h. The solution was concentrated in vacuo at below 30° C. and the residue treated with triethylorthoformate (50 ml) and pyridine (5 ml) and the heterogenous mixture stirred for 18 h at room temperature, followed by heating under reflux for 1.5 h. The mixture was concentrated in vacuo and the residue treated with potassium carbonate solution (30 ml) and extracted with ethyl acetate (2×40 ml). The combined extracts were dried ($Na_2SO_4$) and concentrated in vacuo to leave a dark red oil, which was chromatographed on silica gel eluting initially with ether, then with 1:1 ethyl acetate/ether to afford the title compound (D30) as a yellow oil (430 mg, 15%).

$^1$H NMR ($CDCl_3$, 250 MHz) δ: 1.18 (3H, t, J=7 Hz), 2.25–2.70 (8H, m), 2.40 (3H, s), 3.45 (2H, s), 4.15 (2H, q, J=7 Hz), 7.20–7.40 (5H, m), 8.12 (1H, s).

DESCRIPTION 31

1-Benzyl-4-hydroxymethyl-4-(3-methyl-1,2,4-triazol-1-yl)piperidine (D31)

The title compound (D31) was prepared from ethyl 1-benzyl-4-(3-methyl-1,2,4-triazol-1-yl)piperidin-4-ylcarboxylate (D30) using the method given in Description 29 as a yellow oil (100%). It was used without purification.

$^1$H NMR ($CDCl_3$, 250 MHz) δ: 1.96–2.12 (2H, m), 2.15–2.43 (4H, m), 2.31 (3H, s), 2.58–2.70 (2H, m), 3.47 (2H, s), 3.70 (2H, s), 4.17 1H, br.s), 7.20–7.40 (5H, m), 7.97 (1H, s).

EXAMPLE 1

(±) 3-(3-Methylpyrazol-1-yl)-1-azabicyclo[2.2.2]octane oxalate salt (E1)

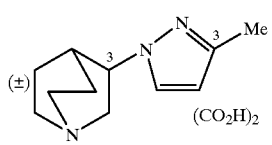

(E1)

3-Quinuclidinyl-hydrazine (D2) (1.0 g, 7.1 mmol) was dissolved in EtOH (4 ml) and glacial acetic acid (4 ml) added followed by acetylacetaldehyde dimethyl acetal (4 ml). The mixture was heated with stirring at reflux for 2 h and evaporated to dryness under reduced pressure. Saturated aqueous potassium carbonate (40 ml) was added and the solution extracted with diethyl ether (3×250 ml). The organic extracts were dried ($Na_2SO_4$), filtered and evaporated to dryness under reduced pressure to yield a brown oil, which was purified by column chromatography (basic alumina, eluting with 10% $Et_2O$/EtOAc) to afford a yellow oil (400 mg, 27%). This was crystallised as the oxalate salt and recrystallised from methanol/ether, m.p. 106–109° C.

$^1$H nmr oxalate salt ($d_6$ DMSO, 270 MHz); 1.72 (2H, m), 1.95 (2H, m), 2.21 (3H, s, pyrazole-Me), 2.30 (1H, m), 3.26 (3H, m), 3.42 (1H, m), 3.82 (2H, bm), 4.78 (1H, m), 6.13 (1H, d, pyrazole-CH), 7.79 (1H, d, pyrazole-CH); $^{13}$C nmr ($d_6$ DMSO, 67 MHz); 13.5, 17.5, 21.4, 26.8, 45.2, 45.7, 49.1, 54.3, 105.4 (pyrazole-CH), 130.6 (pyrazole-CH), 147.2 (oxalate), 163.5 (pyrazole-quat C). MS: $C_{11}H_{17}N_3$: M$^+$ 191; Analysis: $C_{11}H_{17}N_3$. 1.5 $C_2H_2O_4$; % required C, 51.53; H, 6.13; H, 12.88; % found: C, 51.41; H, 6.10; N, 12.74

EXAMPLE 2

(±) 3-(Pyrazol-1-yl)-1-azabicyclo[2.2.2]octane dihydrochloride salt (E2)

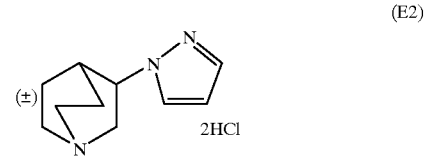

(E2)

3-Quinuclidinyl-hydrazine (D2) (1.0 g, 7.1 mmol) was dissolved in EtOH (4 ml) and glacial acetic acid (4 ml) added, followed by malonaldehyde bis(dimethylacetal) (4 ml). The solution was heated at reflux for 2 h and then evaporated to dryness under reduced pressure. The residue was dissolved in saturated aqueous $K_2CO_3$ and extracted with diethyl ether (3×250 ml). The organic extracts were dried ($Na_2SO_4$), filtered and evaporated to dryness under reduced pressure to yield a brown oil which was purified by column chromatography (basic alumina eluting with ether to EtOAc). The resulting oil was crystallised as the dihydrochloride salt from ether and recrystallised from methanol/ether to yield a white crystalline solid (84 mg), m.p. 192–194° C. (hygroscopic).

$^1$H mnr ($d_6$ DMSO, 270 MHz); 1.85 (2H, bm), 2.04 (3H, bm), 2.25 (1H, m), 2.41 (1H, m), 3.40 (2H, bm), 3.94 (2H, m), 5.02 (1H, m), 6.47 (1H, t, pyrazole-CH), 7.6 (1H, d, pyrazole-CH), 8.08 (1H, d, pyrazole-CH). $^{13}$C nmr ($d_6$ DMSO, 67 MHz); 17.4 ($CH_2$), 20.2 ($CH_2$), 21.3 ($CH_2$), 27.0 (CH), 45.5 ($CH_2$), 48.9 ($CH_2$), 54.6 (CH), 106.0 (CH, pyrazole), 130.1 (CH, pyrazole), 138.8 (CH, pyrazole). MS: $C_{10}H_{15}N_3$. M$^+$: 177; Analysis: $C10H_{15}N_3$. HCl.$H_2$O.MeOH; % required: C, 48.73; H, 6.77; N, 14.21; % found: C, 48.43; H, 6.86; N, 14.44

EXAMPLES 3 and 4

(±) 3-(3-Aminopyrazol-1-yl)-1-azabicyclo[2.2.2]octane (E3) and

(±) 3-(5-aminopyrazol-1-yl)-1-azabicyclo[2.2.2]octane (E4)

(E3)

(E4)

3-Quinuclidinyl-hydrazine (D2) (5.0 g, 35.5 mmol) was added to a solution of $K_2CO_3$ (4.90 g, 35.5 mmol) in water (13 ml) and the ice-cooled solution was stirred vigorously while 2-chloroacrylonitrile (3.10 g, 2.83 ml, 35.5 mmol) was added dropwise over 1 minute. The solution was then stirred at room temperature overnight. The mixture was diluted with MeOH, evaporated to a slurry under reduced pressure, suspended in saturated aqueous potassium carbonate and extracted with EtOAc (3×100 ml), followed by CHCl₃ (4×250 ml). The organic extracts were dried (Na₂SO₄), filtered and evaporated to dryness under reduced pressure to yield a brown oil, which was purified by column chromatography (neutral alumina eluting with chloroform), to yield a faster running fraction (E3) (44 mg) and a slower running fraction (E4) (32 mg). Both were crystallised separately by trituration with diethyl ether, to yield white crystalline solids.

(E3) m.p. 141–145° C.; $^1$H nmr (d$_6$ DMSO, 270 MHz); 1.25 (1H, m), 1.72 (3H, m), 1.97 (1H, m), 2.82 (3H, m), 3.15 (2H, m), 3.72 (1H, dd), 4.26 (1H, m), 5.42 (1H, d, pyrazole-CH), 7.15 (1H, d, pyrazole-CH). $^{13}$C nmr (d$_6$ DMSO, 67 MHz); 19.54 (CH$_2$), 25.45 (CH$_2$), 26.34 (CH), 46.55 (CH$_2$), 46.83 (CH$_2$), 50.68 (CH$_2$), 52.06 (CH), 89.40 (CH, pyrazole), 136.60 (CH, pyrazole), 145.55 (quat C, pyrazole). MS: C$_{10}$H$_{16}$N$_4$ requires 192.1365; observed 192.1377

(E4) m.p. 112–115° C.; $^1$H nmr (d$_6$ DMSO, 270 MHz); 1.26 (1H, m), 1.60 (3H, m), 1.98 (1H, m), 2.68 (3H, m), 2.88 (1H, m), 3.19 (2H, m), 4.08 (1H, m), 5.42 (1H, d, pyrazole-CH), 7.43 (1H, d, pyrazole-CH). $^{13}$C nmr (d$_6$ DMSO, 67 MHz); 20.18 (CH$_2$), 25.75 (CH$_2$), 27.65 (CH), 46.48 (CH$_2$), 46.85 (CH$_2$), 51.81 (CH$_2$), 57.06 (CH), 91.67 (CH, pyrazole), 129.10 (CH, pyrazole), 154.84 (quat C, pyrazole). Analysis: C$_{10}$H$_{16}$N$_4$.⅓ H$_2$O; % required: C, 60.61; H, 8.42; N, 28.28; % found: C, 60.90; H, 8.12; N, 28.48; MS: C$_{10}$H$_{16}$N$_4$ required 192.1374; observed 192.1375

EXAMPLE 5

3-(3-Methyl-1,2,4-triazol-1-yl)-1-azabicyclo[2.2.2]oct-2-ene dihydrochloride (E5)

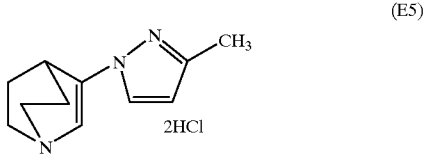

3-Quinuclidinyl-hydrazone (D1) (0.20 g, 1.44 mmol) was dissolved in dry MeOH (10 ml) and methyl acetimidate hydrochloride (0.158 g, 1.45 mmol) added, followed by triethylamine (0.2 ml, 1 eq). The clear solution was stirred for 3 h under N$_2$, evaporated to dryness under reduced pressure, and anhydrous pyridine (2 ml) and anhydrous triethylorthoformate (20 ml) added. The suspension was stirred under N$_2$ overnight at room temperature and then heated at reflux for 1 h. The resulting yellow suspension was evaporated to dryness under reduced pressure, dissolved in saturated, aqueous potassium carbonate and extracted with EtOAc (3×70 ml). The organic extracts were dried (Na₂SO₄), filtered and evaporated to dryness under reduced pressure. The resulting orange semi-solid was purified by Kugelröhr distillation (b.p. 180° C. at 0.08 mmHg) to yield a clear colourless oil (171 mg, 63%) which was purified as the dihydrochloride salt, m.p. 212–214° C. (decomp.).

$^1$H nmr (d$_6$ DMSO, 270 MHz); 2.00 (2H, bm), 2.18 (2H, bm), 2.49 (3H, triazole-Me), 3.20 (2H, m), 3.71 (2H, m), 4.02 (1H, m), 7.19 (1H, s, olefinic-CH), 9.28 (1H, s, triazole-CH). $^{13}$C nmr (d$_6$ DMSO, 67 MHz); 13.7 (CH$_3$-triazole), 23.0 (CH$_2$), 26.8 (CH), 50.0 (CH$_2$), 114.5 (olefinic CH), 142.0 (quat-C), 144.8 (triazole-CH) 161.8 (quat-C). MS: C$_{10}$H$_{14}$N$_4$ M$^+$: 190; Analysis: C$_{10}$H$_{14}$N$_4$. 2HCl; % requires: C, 45.62; H, 6.08; N, 21.29; % found: C, 45.41; 6.12; N, 21.27

EXAMPLE 6

(±) 3-(3-Methyl-1,2,4-triazol-1-yl)-1-azabicyclo[2.2.2] octane dihydrochloride salt (E6)

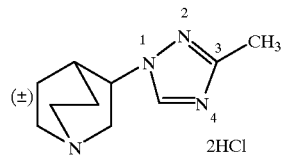

3-Quinuclidinyl-hydrazine dihydrochloride (D5) (0.78 g, 3.6 mmol) was suspended in dry methanol (30 ml) and methyl acetimidate hydrochloride (0.40 g, 3.65 mmol) added, followed by triethylamine (1.52 ml, 3 eq). The solution was stirred for 3 h at room temperature under N$_2$, and then evaporated to dryness under reduced pressure at a temperature not exceeding 30° C. Anhydrous triethylorthoformate (40 ml) and anhydrous pyridine (4 ml) were added, and the suspension was stirred overnight at room temperature under N$_2$ and then refluxed under N$_2$ for 1.5 h. The mixture was cooled, evaporated to dryness under reduced pressure and the residue was dissolved in saturated aqueous potassium carbonate solution (40 ml). The solution was extracted with ethyl acetate (2×300 ml), the organic extracts dried (Na₂SO₄), filtered and evaporated to dryness under reduced pressure. The resulting oil was purified by column chromatography using neutral alumina and with gradient elution using ethyl acetate to 2% methanol in ethyl acetate. The resulting clear oil was crystallised as the dihydrochloride salt using diethyl ether/methanol solution and recrystallised in acetone/ether to afford the title compound as white crystals (110 mg, 13%), m.p. >250° C.

$^1$H nmr (d$_6$ DMSO, 270 MHz); 1.85 (2H, bm), 2.04 (2H, bm), 2.42 (3H, s, Me), 2.50 (1H, m), 3.40 (4H, bm), 3.80 (2H, bm), 5.07 (1H, m), 9.05 (1H, s, triazole CH). $^{13}$C nmr (d$_6$ DMSO, 67 MHz); 13.1 (CH$_3$), 17.2 (CH$_2$), 21.3 (CH$_2$), 26.0 (CH), 45.0 (CH$_2$), 45.5 (CH$_2$), 48.9 (CH$_2$), 53.4 (CH), 143.9 (triazole-CH), 157.0 (triazole quat C). MS: C$_{10}$H$_{16}$N$_4$ requires 192.1374; observed 192.1375; Analysis: C$_{10}$H$_{18}$N$_4$.Cl$_2$; % required: C, 45.29; H, 6.84; N, 21.13; % found: C, 44.99; H, 6.93; N, 20.82

EXAMPLE 7

(±) 3-(1,2,4-Triazol-1-yl)-1-azabicyclo[2.2.2]octane dihydrochloride salt (E7)

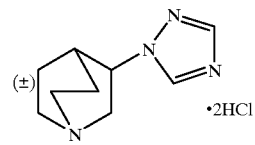

3-Quinuclidyl-hydrazine dihydrochloride salt (D5) (200 mg, 1.0 mmol) and Gold's reagent ([3-(dimethylamino)-2-azaprop-2-en-1-ylidene]-dimethylammonium chloride) (153 mg, 1.0 mmol) were dissolved in dry CHCl₃ (20 ml) under N₂ and dry Et₃N (0.28 ml, 2.0 mmol) was added. The solution was heated at reflux under nitrogen for 2.5 h. The solution was cooled, saturated aqueous potassium carbonate was added and the organic layer separated. The aqueous layer was extracted with CHCl₃ (2×100 ml), the organic extracts were dried (Na₂SO₄), filtered and were evaporated to dryness under reduced pressure. The resulting orange/yellow oil was purified by column chromatography (basic alumina eluting with 2% MeOH/EtOAc). The resulting clear oil was recrystallised as the dihydrochloride salt from methanol/acetone/diethyl ether (45 mg, 0.18 mmol, 18%), m.p. 187–190° C.

$^1$H NMR (d₆ DMSO, 270 MHz); 1.83 (2H, m), 1.99 (2H, m), 2.42 (1H, m), 3.29 (4H, bm), 3.86 (2H, bm), 5.08 (1H, m), 8.28 (1H, s, triazole-CH), 9.02 (1H, s, triazole-CH). $^{13}$C NMR (d₆ DMSO, 67 MHz); 17.1 (CH₂), 21.2 (CH₂), 26.5 (CH), 44.8 (CH₂), 45.2 (CH₂), 49.0 (CH₂), 53.3 (CH), 144.0 (triazole-CH), 150.2 (triazole-CH); MS: C₉H₁₄N₄ requires 178.1206; M⁺ observed 178.1221; Analysis: C₉H₁₄N₄. 2HCl; % requires C, 43.0; H, 6.4; N, 22.3; found C, 42.97; H, 6.48; N, 22.23

EXAMPLE 8

(±) exo-3-(3-Methyl-1,2,4-triazol-1-yl)-1-azabicyclo-[2.2.1]heptane dihydrochloride salt (E8)

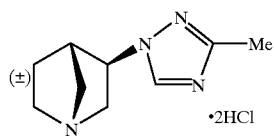

(E8)

(±) exo and endo (1-Azabicyclo[2.2.1]heptan-3-yl)-hydrazine dihydrochloride (D7) (0.5 g, 2.5 mmol) was dissolved in dry methanol (30 ml) and methyl acetimidate hydrochloride (0.274 g, 2.5 mmol) was added, followed by dry triethylamine (1.05 ml, 3 eq). The solution was stirred for 3 h at 25° C. under N₂, and then evaporated to dryness under reduced pressure at a temperature not exceeding 30° C. Anhydrous triethylorthoformate (20 ml) and anhydrous pyridine (2 ml) were added, and the suspension was stirred overnight at room temperature and then heated at reflux under N₂ for 1.5 h. The mixture was cooled, evaporated to dryness under reduced pressure, and the residue dissolved in saturated aqueous K₂CO₃. The aqueous solution was extracted with ethyl acetate (3×250 ml) and the organic extracts were dried, filtered and evaporated to dryness under reduced pressure to yield a yellow oil which was purified by column chromatography (basic alumina, eluting with EtOAc/MeOH 3–6%). The compound thus isolated was crystallised from ether as the dihydrochloride salt and was recrystallised from methanol/diethyl ether to afford the title compound (E8) as a white crystalline solid (30 mg, 0.12 mmol, 5%) m.p. 236–240° C. (decomp).

$^1$H NMR (d₆ DMSO, 270 MHz); 1.75 (1H, m), 2.08 (1H, m), 2.31 (3H, s, triazole-CH₃), 3.14 (1H, d), 3.28 (3H, complex m), 3.63 (2H, m), 3.82 (1H, m), 4.92 (1H, m), 8.90 (1H, s, triazole-CH); $^{13}$C (d₆ DMSO, 67 MHz); 13.1 (CH₃-triazole), 24.3 (CH₂), 41.7 (CH), 51.0 (CH₂), 56.8 (CH₂), 57.3 (CH₂), 58.4 (CH), 143.9 (CH, triazole-CH), 158.7 (quat-C)

EXAMPLE 9

(±) exo-3-(1,2,4-Triazol-1-yl)-1-azabicyclo[2.2.1]heptane dihydrochloride salt (E9)

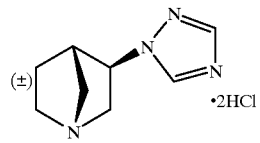

(E9)

(±) exo and endo(1-Azabicyclo[2.2.1]heptan-3-yl)-hydrazine dihydrochloride (D7) (500 mg, 2.5 mmol) and Gold's reagent ([3-(dimethylamino)-2-azaprop-2-en-1-ylidine]dimethylammonium chloride) (409 mg, 2.5 mmol) were dissolved in dry CHCl₃ (40 ml) under N₂ and dry triethylamine (0.70 ml, 2 eq) added. The solution was heated at reflux under N₂ for 2.5 h. The solution was cooled, saturated aqueous potassium carbonate was added and the organic layer separated. The aqueous layer was extracted with CHCl₃ (2×100 ml) and the organic solutions were dried (Na₂SO₄), filtered and evaporated to dryness under reduced pressure to yield a yellow oil (0.5 g). This was purified by column chromatography (basic alumina, eluting with EtOAc/MeOH 2%) to yield a clear colourless oil which was crystallised as the dihydrochloride salt and recrystallised from methanol/diethyl ether to afford the title compound (E9) as pale yellow crystals, m.p. 215–219° C. (decomp).

$^1$H NMR (d₆ DMSO, 270 MHz); 1.86 (1H, m), 2.16 (1H, m), 3.20–4.03 (7H, complex m), 5.12 (1H, m), 8.42 (1H, bs, triazole-CH), 9.21 (1H, bs, triazole-CH). $^{13}$C NMR (d₆ DMSO, 67 MHz); 24.3 (CH₂), 41.8 (CH), 50.9 (CH₂), 56.7 (CH₂), 57.3 (CH₂), 58.6 (CH), 150.0 (2C-triazole-2CH)

EXAMPLE 10

(±) 3-(5-Methyltetrazol-2-yl)-1-azabicyclo[2.2.2]octane hydrochloride salt (E10)

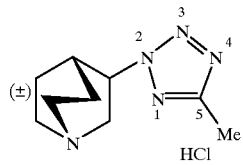

(E10)

3-Methanesulphonyloxy-1-azabicyclo[2.2.2]octane (D8) (1.0 g, 4.9 mmol) was dissolved in dry DMF (50 ml) and the sodium salt of 5-methyltetrazole (D17) (1.26 g, 2.5 eq) was added, and the solution was refluxed for 1 h under nitrogen. The solution was evaporated to dryness under reduced pressure, and the resulting syrup dissolved in aqueous saturated potassium carbonate solution (50 ml). The aqueous solution was extracted with EtOAc (3×100 ml), the organic extracts dried (Na₂SO₄), filtered and evaporated to dryness under reduced pressure to yield an oil. This was purified by column chromatography using basic alumina and eluting with EtOAc/MeOH 1–5%, to yield the free base of the title compound (E10) (90 mg, 10%), which was crystallised using 1.0M HCl in ether solution as the hydrochloride salt, m.p. 196–198° C.

$^1$H NMR (d₆ DMSO, 270 MHz); 1.63 (1H, m), 1.79 (1H, m), 2.05 (2H, m), 2.50 (3H, s, azole-CH₃), 3.32 (5H, m), 3.92 (2H, m), 5.44 (1H, m, CH-azole); $^{13}$C NMR; 10.6 (CH$_3$), 17.1 (CH$_2$), 20.9 (CH$_2$), 25.6 (CH), 45.1 (CH$_2$), 45.5 (CH$_2$), 49.0 (CH$_2$), 57.1 (CH), 162.4 (azole quat-C); MS: found 199.1328; C$_9$H$_{15}$N$_5$ requires 199.1328; Analysis C$_9$H$_{15}$N$_5$.HCl ¼H$_2$O; found C: 46.53; H: 6.96; N: 29.45%; requires C: 46.15; H: 7.05; N: 29.91%

EXAMPLE 11

(±) 3-(5-Aminotetrazol-2-yl)-1-azabicyclo[2.2.2]octane (E11)

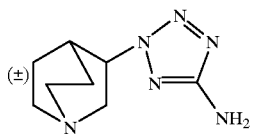

(E11)

3-Methanesulphonyloxy-1-azabicylo[2.2.2]octane (D8) (2.0 g, 9.7 mmol) and the sodium salt of 5-aminotetrazole (D15) (2.5 g, 2.0 eq) were dissolved in dry DMF (50 ml) and the reaction carried out as for Example 10. The product (E11) isolated from column chromatography was a white crystalline solid (124 mg, 6.6%), which was recrystallised from ether, m.p. 132–134° C.

$^1$H NMR (CDCl$_3$, 270 MHz); 1.42 (1H, m), 1.68 (3H, complex m), 2.35 (1H, m), 2.87 (1H, m), 3.11 (1H, m), 3.39 (1H, dm), 3.71 (1H, dt), 4.38 (2H, bs, NH$_2$), 4.70 (1H, m, CH-azole). $^{13}$C NMR; 20.4 (CH$_2$), 26.0 (CH$_2$), 27.6 (CH), 47.2 (CH$_2$), 47.5 (CH$_2$), 52.1 (CH$_2$), 61.3 (CH), 166.1 (azole quat C). MS found 194.1282; C$_8$H$_{14}$N$_6$ requires 194.1280; Analysis C$_8$H$_{14}$N$_6$.¼H$_2$O; Found: C: 47.76; H; 6.82; N: 40.79%; Required: C: 47.23; H: 7.38; N: 41.33%

EXAMPLES 12 TO 14

(±) 3-(4-Methyl-1,2,3-triazol-2-yl)-1-azabicyclo-[2.2.2]octane hydrochloride (E12)

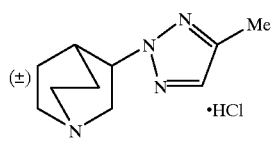

(E12)

3-Methanesulphonyloxy-1-azabicyclo[2.2.2]octane (D8) (5.0 g, 24.4 mmol) and the sodium salt of 4-methyl-1,2,3-triazole (D21) (5.0 g, 2 equivs) were dissolved in dry DMF (150 ml) and the reaction carried out as in Example 10. The compound first eluted by column chromatography was the free base of the title compound (E12), (1.1 g, 23.5%), which was crystallised as a hydrochloride salt to give the title compound (E12) (m.p. 181–182° C.).

$^1$H NMR (d$_6$DMSO, 270 MHz); 1.50 (1H, m), 1.70 (1H, m), 1.98 (2H, m), 2.27 (3H, s, azole-Me), 3.24 (4H, bm), 3.38 (1H, m), 3.87 (2H, m), 5.08 (1H, m), 7.68 (1H, s, azole-H). $^{13}$C NMR (d$_6$ DMSO); 10.4 (CH$_3$), 17.3 (CH$_2$), 20.9 (CH$_2$), 26.0 (CH), 45.1 (CH$_2$), 45.4 (CH$_2$), 48.9 (CH$_2$), 57.5 (CH), 133.8 (CH-azole), 143.8 (azole quat C). MS: Found 192.1373; C$_{10}$H$_{16}$N$_4$ requires 192.1375; Analysis: C$_{10}$H$_{16}$N$_4$.HCl ¼H$_2$O; Found: C: 51.38; H: 7.34; N: 24.02%; Required: C: 51.50; H: 7.51; N: 24.00%

Also isolated were the isomers 3-(4-methyl-1,2,3-triazol-3-yl)-1-azabicyclo[2.2.2]octane (E13) and 3-(4-methyl-1,2,3-triazol-1-yl)-1-azabicyclo[2.2.2] octane (E14) which were both crystallised as oxalate salts, (E13) m.p. 151–153° C., (E14) m.p. 135–140° C.

(E13) $^1$H NMR (CDCl$_3$, 270 MHz); 1.75 (2H, tm), 2.08 (2H, bm), 2.36 (1H, m), 2.41 (3H, s, azole-Me), 3.33 (3H, m), 3.52 (1H, m), 3.81 (1H, tm), 5.05 (1H, m, CH-azole), 7.68 (1H, s, azole-H). $^{13}$C NMR (CDCl$_3$); 7.8 (CH$_3$), 17.5 (CH$_2$), 22.1 (CH$_2$), 25.7 (CH), 45.5 (CH$_2$), 45.8 (CH$_2$), 49.6 (CH$_2$), 52.0 (CH), 132.9 (C-H-azole), 133.8 (azole quat C). MS: found 192.1377; C$_{10}$H$_{16}$N$_4$ requires 192.1375;

(E14) $^1$H NMR (d$_6$ DMSO, 270 MHz); 1.66 (1H, m), 1.82 (1H, m), 2.10 (2H, m), 2.35 (3H, s, azole-Me), 2.50 (1H, m), 3.40 (4H, m), 3.94 (1H, m), 4.07 (1H, m), 5.20 (1H, m, CH-azole), 8.18 (1H, s, azole-H). $^{13}$C NMR (d$_6$ DMSO); 10.5 (CH$_3$), 17.2 (CH$_2$), 21.3 (CH$_2$), 26.5 (CH), 45.2 (CH$_2$), 45.4 (CH$_2$), 48.8 (CH$_2$), 54.1 (CH), 122.5 (CH-azole), 142.5 (azole quat-C) MS Found 192.1377; C$_{10}$H$_{16}$N$_4$ requires 192.1375

EXAMPLES 15 AND 16

(±) 3-(Tetrazol-2-yl)-1-azabicyclo[2.2.2]octane hydrochloride salt (E15)

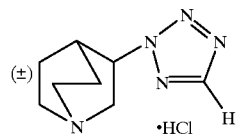

(E15)

(±) 3-(Tetrazol-1-yl)-1-azabicyclo[2.2.2]octane hydrochloride salt (E16)

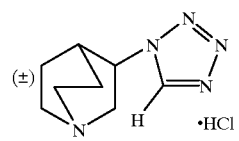

(E16)

3-Methanesulphonyloxy-1-azabicyclo[2.2.2]octane (D8) (1.0 g, 4.9 mmol) was dissolved in dry DMF (50 ml) and the sodium salt of 1H-tetrazole (D16) (1.5 g, 3.4 eq) was added. The reaction was carried out as in Example 10 to yield two separate compounds by column chromatography, the faster running compound being the free base of E15 (80 mg, 9%) and the slower running compound being the free base of E16 (60 mg, 7%). Both compounds were crystallised as the hydrochloride salts, E15 m.p. 177–180° C. and E16 m.p. 229–230° C.

(E15) $^1$H NMR (d$_6$ DMSO, 270 MHz); 1.68 (1H, m), 1.91 (1H, m), 2.19 (2H, m), 2.75 (1H, m), 3.42 (4H, m), 4.06 (2H, m), 5.66 (1H, m, CH-azole), 9.21 (1H, s, azole-H). $^{13}$C NMR (d$_6$ DMSO); 17.1 (CH$_2$), 20.9 (CH$_2$), 25.7 (CH), 45.1 (CH$_2$), 45.4 (CH$_2$), 49.0 (CH$_2$), 57.4 (CH), 153.4 (azole C-H). MS found 179.1173; C$_8$H$_{13}$N$_5$ requires 179.1171; Analysis: C$_8$H$_{13}$N$_5$.HCl; Found: C: 44.10; H: 6.43; N: 32.00%; Required: C: 44.5; H: 6.5; N: 32.5%

(E16) $^1$H NMR (d$_6$DMSO, 270 MHz); 2.00 (2H, m), 2.52 (2H, m), 3.12 (1H, m), 3.43 (6H, complex m), 5.35 (1H, m, CH-azole), 9.08 (1H, s, azole-H). $^{13}$C NMR (d$_6$ DMSO); 21.8 (CH$_2$), 22.8 (CH$_2$), 38.6 (CH), 49.6 (CH$_2$), 50.1 (CH$_2$), 56.2 (CH$_2$), 60.2 (CH), 153.1 (azole quat C). MS found 179.1171; $C_8H_{13}N_5$ requires 179.1171; Analysis $C_8H_{13}N_5 \cdot HCl \cdot \frac{1}{3} H_2O$; Found: C: 43.86; H: 6.38; N: 31.18%; Required: C: 43.34; H: 6.62; N: 31.60%

EXAMPLE 17

(±) exo-3-(5-Aminotetrazol-2-yl)-1-azabicyclo[3.2.1] octane hydrochloride (E17)

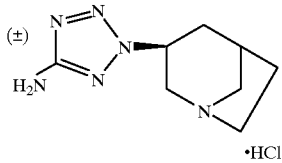
(E17)

endo-3-Methanesulphonyloxy-1-azabicyclo[3.2.1]octane (D12) (600 mg, 2.94 mmol) and the sodium salt of 5-aminotetrazole (D15) (405 mg, 1.5 equiv) were dissolved in dry DMF (30 ml) and the reaction carried out as for Example 10. The fraction eluted first from column chromatography (basic alumina, EtOAc/MeOH 1–2%) was the free base of the title compound which was purified as the hydrochloride salt (205 mg, 30%) m.p. 262–264° C. (decomp).

$^1$H NMR ($d_6$DMSO); 2.19 (3H, m), 2.34 (1H, m), 2.88 (1H, s), 3.50 (5H, complex m), 3.85 (1H, m), 5.35 (1H, m, CH-azole). $^{13}$C NMR ($d_6$DMSO); 26.4 ($CH_2$), 32.6 (CH), 34.1 ($CH_2$), 50.3 ($CH_2$), 52.6 (CH), 53.2 ($CH_2$), 57.3 ($CH_2$), 167.0 (azole quat carbon) MS: found 194.1280; $C_8H_{14}N_6$ requires 194.1280; Analysis: $C_8H_{14}N_6 \cdot HCl \cdot \frac{1}{8} H_2O$; Found: C: 41.52; H: 6.63; N: 35.86% Required: C: 41.25; H: 6.55; N: 36.09%

EXAMPLE 18

(±) exo-3-(5-Aminotetrazol-2-yl)-1-azabicyclo[2.2.1] heptane (E18)

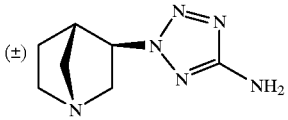
(E18)

endo-3-Methanesulphonyloxy-1-azabicyclo[2.2.1]heptane (D10) (0.7 g, 3.66 mmol) and the sodium salt of 5-aminotetrazole (D15) (1.0 g, 2.6 equiv) were dissolved in dry DMF (50 ml) and the reaction carried out as in Example 10. The product isolated from column chromatography was a white crystalline solid (70 mg, 10.6%), which was recrystallised from ether to give the title compound (E18) (m.p. 132–134° C.).

$^1$H NMR (CDCl$_3$, 270 MHz); 1.29 (1H, m), 1.77 (1H, m), 2.50 (2H, m), 2.88 (1H, tm), 3.06 (3H, complex m), 3.32 (1H, dm), 4.36 (2H, bs, NH$_2$), 4.44 (1H, m, CH-azole). $^{13}$C NMR (CDCl$_3$); 27.9 (CH$_2$), 43.4 (CH), 53.7 (CH$_2$), 58.3 (CH$_2$), 61.6 (CH$_2$), 65.8 (CH), 165.9 (azole quat C); MS found 180.1121 $C_7H_{12}N_6$ requires 180.1123; Analysis $C_7H_{12}N_6$; Found C: 46.43; H, 6.71; N: 46.17%; Required C: 46.65; H: 6.71; N: 46.63%

EXAMPLE 19

(±) exo-3-(Tetrazol-2-yl)-1-azabicyclo[2.2.1]heptane hydrochloride salt (E19)

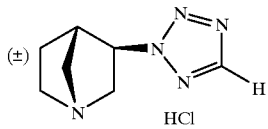
(E19)

endo-3-Methanesulphonyloxy-1-azabicyclo[2.2.1] heptane (D10) (0.70 g, 3.66 mmol) and the sodium salt of 1H-tetrazole (D16) (1.0 g, 3 equiv) were dissolved in dry DMF (50 ml) and the reaction carried out as in Example 10. The resulting product eluted first from column chromatography was a pale yellow oil (70 mg, 12%), which was crystallised to give the title compound (E19) as the hydrochloride salt (m.p. 241–245° C.)

$^1$H NMR ($d_6$DMSO, 270 MHz); 1.92 (1H, m), 2.12 (1H, m), 3.32 (4H, complex), 3.50 (1H, d), 3.84 (1H, dm), 4.00 (1H, dm), 5.51 (1H, m), 9.1] (1H, s, azole-H). $^{13}$C NMR ($d_6$DMSO); 23.9 (CH$_2$), 41.6 (CH), 51.2 (CH$_2$), 56.8 (CH$_2$), 57.5 (CH$_2$), 62.1 (CH), 153.4 (azole-CH). MS: Found 165.1010; $C_7H_{11}N_5$ requires 165.1006; Analysis $C_7H_{11}N_5 \cdot HCl$; Found: C: 41.54; H: 6.04; N: 34.43%; Required: C: 41.69; H: 6.00; N: 34.73%

EXAMPLES 20 and 21

(±) exo-3-(5-Methyltetrazol-2-yl)-1-azabicyclo[2.2.1] heptane hydrochloride salt (E20)

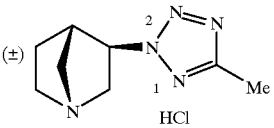
(E20)

(±) exo-3-(5-Methyltetrazol-1-yl)-1-azabicyclo[2.2.1] heptane hydrochloride salt (E21)

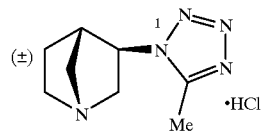
(E21)

endo-3-Methylsulphonyloxy-1-azabicyclo[2.2.1]heptane (D10) (0.7 g, 3.66 mmol) and the sodium salt of 5-methyltetrazole (D17) (0.8 g, 2 eq) were dissolved in dry DMF (50 ml), and the reaction carried out as in Example 10. The compound first eluted by column chromatography was the free base of E20 (90 mg, 14%) and was crystallised as the HCl salt (E20) (m.p. 238–239° C.). The compound subsequently eluted was the free base of E21 (50 mg, 7.6%), which was crystallised as the hydrochloride salt (E21) (m.p. 246–248° C.).

(E20), $^1$H NMR ($d_6$DMSO, 270 MHz); 1.93 (1H, m), 2.14 (1H, m), 2.50 (3H, s, azole-Me), 3.38 (5H, complex m), 3.81 (1H, dt), 4.00 (1H, m), 5.43 (1H, m, CH-azole); $^{13}$C NMR (d$_6$DMSO); 10.5 (CH$_3$), 23.9 (CH$_2$), 41.6 (CH), 51.1 (CH$_2$), 56.8 (CH$_2$), 57.4 (CH$_2$), 61.9 (CH), 162.5 (quat azole-C). MS found 179.1173; C$_8$H$_{13}$N$_5$ requires 179.1171; Analysis C$_8$H$_{13}$N$_5$.HCl ¼H$_2$O; Found: C: 43.84; H: 6.43; N: 31.72%; Required: C: 43.64; H: 6.59; N: 31.82%

(E21); $^1$H NMR (d$_6$DMSO, 270 MHz); 1.97 (1H, m), 2.19 (1H, m), 2.65 (3H, s, azole-Me), 3.44 (4H, complex m), 3.70 (1H, d), 3.82 (1H, dt), 3.98 (1H, m), 5.10 (1H, m, CH-azole). $^{13}$C NMR (d$_6$DMSO); 8.6 (CH$_3$), 24.3 (CH$_2$), 41.5 (CH), 51.2 (CH$_2$), 56.4 (CH), 57.0 (CH$_2$), 58.1 (CH$_2$), 152.6 (quat azole-C). MS found 179.1171; C$_8$H$_{13}$N$_5$ requires 179.1171; Analysis C$_8$H$_{13}$N$_5$.HCl; Found: C: 44.68; H: 6.56; N: 32.48%; Required: C: 44.55; H: 6.54; N: 32.47

EXAMPLE 22

(±) exo-3-(Tetrazol-2-yl)-1-azabicyclo[3.2.1]octane hydrochloride salt (E22)

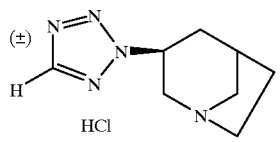

(E22)

endo-3-Methanesulphonyloxy-1-azabicyclo[3.2.1] octane (D12) (600 mg, 2.94 mmol) and the sodium salt of 1H-tetrazole (D16) (405 mg, 1.5 equiv) were dissolved in dry DMF (30 ml) and the reaction carried out as for Example 10. The fraction eluted first by column chromatography (basic alumina, EtOAc/MeOH 1–2%) was the free base of the title compound which was purified as the hydrochloride salt (170 mg, 27%) m.p. 232–234° C.

$^1$H NMR (d$_6$DMSO); 2.28 (3H, m), 2.50 (1H, m), 2.97 (1H, s), 3.31 (1H, m), 3.53 (2H, m), 3.80 (2H, m), 4.02 (1H, m), 5.72 (1H, m, CH-azole), 9.22 (1H, s, azole-H). $^{13}$C NMR (d$_6$DMSO); 26.6 (CH$_2$), 32.9 (CH), 34.5 (CH$_2$), 50.7 (CH$_2$), 53.4 (CH$_2$), 53.7 (CH), 57.6 (CH$_2$), 153.6 (azole quat carbon). MS: found 179.1168; C$_8$H$_{13}$N$_5$ requires 179.1171; Analysis: C$_8$H$_{13}$N$_5$.HCl; Found: C: 44.51; H: 6.59; N: 32.31%; Required: C: 44.55; H: 6.54; N: 32.47

EXAMPLES 23 and 24

(±) exo-3-(5-Ethyltetrazol-2-yl)-1-azabicyclo[2.2.1] heptane hydrochloride salt (E23)

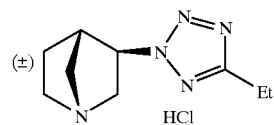

(E23)

endo-3-Methanesulphonyloxy-1-azabicyclo[2.2.1] heptane (D10) (0.82 g, 4.29 mmol) and the sodium salt of 5-ethyltetrazole (D18) (0.60 g, 1.2 equiv) were dissolved in dry DMF (25 ml) and the reaction carried out as in Example 10. The first product eluted from the column was the free base of the title compound (80 mg, 9.7%), which was crystallised as the hydrochloride salt (E23) (m.p. 142–145° C.).

$^1$H NMR (d$_6$DMSO, 270 MHz); 1.28 (3H, t, Et-CH$_3$), 1.89 (1H, m), 2.1] (1H, m), 2.86 (2H, q, Et-CH$_2$), 3.31 (4H, complex m), 3.49 (1H, d), 3.82 (1H, dm), 3.94 (1H, m), 5.39 (1H, m, CH-azole); $^{13}$C NMR (d$_6$DMSO); 12.1 (CH$_3$-ethyl), 18.4 (CH$_2$), 23.9 (CH$_2$), 41.5 (CH), 51.3 (CH$_2$), 56.9 (CH$_2$), 57.6 (CH$_2$) 61.9 (CH), 167.2 (azole quat C) Analysis C$_9$H$_{15}$N$_5$. 1 ½HCl; Found: C: 43.73; H: 6.50; N: 28.15%; Requires: C: 43.60; H: 6.66; N: 28.25%

Also isolated by column chromatography was (±) exo-3-(5-ethyltetrazol-1-yl)-1-azabicyclo[2.2.1]heptane (E24) (80 mg, 9.7%), which was crystallised as the hydrochloride salt (m.p. 268–270° C.).

$^1$H NMR (d$_6$DMSO, 270 MHz); 1.28 (3H, t, ethyl-CH$_3$), 1.90 (1H, m), 2.08 (1H, m), 2.91 (2H, dq, ethyl CH$_2$), 3.31 (4H, complex m), 3.62 (1H, d), 3.72 (1H, dm), 3.88 (1H, dm), 5.00 (1H, m, CH-azole). $^{13}$C NMR (d$_6$DMSO); 10.9 (CH$_3$), 16.1 (CH$_2$), 24.3 (CH$_2$), 41.6 (CH), 51.3 (CH$_2$), 56.2 (CH), 57.1 (CH$_2$), 58.3 (CH$_2$), 156.5 (azole quat C)

EXAMPLE 25

(±) exo-3-(4-Methyl-1,2,3-triazol-2-yl)-1-azabicyclo-[2.2.1]heptane hydrochloride salt (E25)

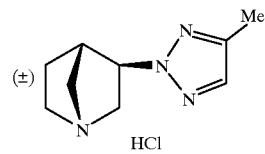

(E25)

endo-3-Methanesulphonyloxy-1-azabicyclo[2.2.1] heptane (D10) (1.0 g, 5.24 mmol) and the sodium salt of 4-methyl-1,2,3-triazole (D21) (1.13 g, 10 mmol) were dissolved in dry DMF (50 ml) and the reaction carried out as for Example 10. The free base of the product was isolated as a clear colourless oil from column chromatography (basic alumina, eluting with EtOAc/MeOH 1–3%), and was crystallised as the hydrochloride salt (250 mg, 22%), m.p. 160–162° C.

$^1$H NMR (d$_6$DMSO); 1.84 (1H, m), 2.06 (1H, m), 2.25 (3H, m, CH$_3$), 3.29 (5H, complex m), 3.82 (2H, m), 5.03 (1H, m, CH-azole), 7.67 (1H, s, azole-H); $^{13}$C NMR (d$_6$DMSO); 10.3 (CH$_3$), 23.9 (CH$_2$), 41.7 (CH), 51.2 (CH$_2$), 56.7 (CH$_2$), 57.3 (CH$_2$), 62.7 (CH), 134.0 (CH), 144.0 (azole quat carbon). MS: found 178.1219; C$_9$H$_{14}$N$_4$ requires 178.1218; Analysis: C$_9$H$_{14}$N$_4$.HCl; Found: C: 50.26; H: 7.08; 26.10%; Required C: 50.35; H: 7.04; N: 25.87%

EXAMPLE 26

(±) endo-3-(5-Aminotetrazol-2-yl)-1-azabicyclo[2.2.1] heptane hydrochloride salt (E26)

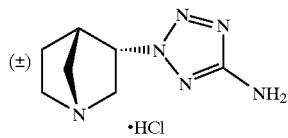

(E26)

exo-3-Methanesulphonyloxy-1-azabicyclo[2.2.1]heptane (D22) (400 mg, 2.1 mmol) and the sodium salt of 5-aminotetrazole (D15) (600 mg, 5.61 mmol) were dissolved in dry DMF (40 ml) and the reaction carried out as in Example 10. The product isolated from column chromatography was a white crystalline solid (60 mg, 16%) which was recrystallised as the hydrochloride salt (E26) containing 18% of the hydrochloride salt of the exo isomer (E18) m.p. 216–218° C. (decomp).

$^1$H NMR (d$_6$DMSO); 1.39 (1H, m), 2.01 (1H, m), 3.48 (4H, complex m), 3.94 (3H, complex m), 5.53 (1H, m, CH-azole). $^{13}$C NMR (d$_6$DMSO); 20.8 (CH$_2$), 40.9 (CH), 51.7 (CH$_2$), 53.5 (CH$_2$), 58.1 (CH$_2$), 60.0 (CH), 167.3 (quat-C). MS found 180.1125; C$_7$H$_{12}$N$_6$ requires 180.1123

EXAMPLE 27

(±) 5-(1,2,4-Triazol-1-yl)-1-azabicyclo[3.2.1]octane dihydrochloride salt (E27)

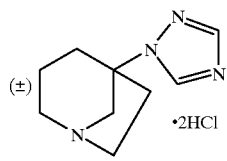

(±) 1-Azabicyclo[3.2.1]oct-5-ylhydrazine (D24, 1.34 g, assumed 5.3 mmol) and Gold's reagent (0.86 g, 5.3 mmol) were heated at reflux in absolute chloroform (75 ml) for 2 h. The reaction mixture was cooled and then partitioned between saturated aqueous potassium carbonate solution (75 ml) and chloroform (4×75 ml). The combined organic extracts were dried (Na$_2$SO$_4$) and evaporated to yield a gum which was chromatographed on alumina using a graded eluant of 0–2% methanol/chloroform to give the triazole as a low-melting solid (0.50 g, 53%). A portion of this material was taken-up in methanol and converted to the dihydrochloride which was recrystallised from methanol/acetone to give the title compound (E27) as a white crystalline solid m.p. 198–200° C.

$^1$H NMR (d$_6$ DMSO) δ: 1.9–2.3 (4H, m), 2.52 (2H, m), 3.30 (2H, m), 3.53 (1H, m), 3.60–3.84 (3H, m), 5.0 (1H, br), 8.30 (1H, s), 9.08 (1H, s), 11.90 (1H, br). $^{13}$C NMR (d$_6$ DMSO) δ: 16.89, 32.01, 34.24, 48.95, 50.96, 58.28, 64.05, 142.50, 150.07. Analysis: C$_9$H$_{14}$N$_4$. 2HCl requires C: 43.02; H: 6.42; N: 22.31; found C: 42.77; H: 6.35; N: 21.86

EXAMPLE 28

(±) 5-(3-Methyl-1,2,4-triazol-1-yl)-1-azabicyclo-[3.2.1]octane dihydrochloride salt (E28)

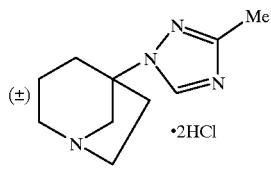

(±) 1-Azabicyclo[3.2.1]oct-5-ylhydrazine (D24, 2.61 g, assumed 10.5 mmol) was treated with methyl acetimidate hydrochloride (1.15 g, 10.5 mmol) and triethylamine (1.5 ml, 10.8 mmol) in dry methanol (75 ml) at room temperature for 3 h. The reaction mixture was then concentrated in vacuo and anhydrous triethylorthoformate (150 ml) and anhydrous pyridine (15 ml) were added. The reaction mixture was stirred at room temperature overnight and then refluxed for 3 h. The resulting mixture was cooled, evaporated to dryness under reduced pressure, and the residue was partitioned between saturated aqueous potassium carbonate solution (100 ml) and chloroform (4×100 ml). The combined organic extracts were dried (Na$_2$SO$_4$) and evaporated to a gum which was chromatographed on silica using 8% methanol/chloroform as eluant to give the methyltriazole as an oil (0.104 g, 5%). A portion of this material was taken up in methanol, converted to the dihydrochloride salt, and recrystallised from methanol/acetone to give the title compound (E28) as a white crystalline solid m.p. 165–167° C.

$^1$H NMR (d$_6$DMSO) δ: 1.91–2.24 (4H, m), 2.21 (3H, s), 2.47 (2H, m), 3.28 (2H, m), 3.48 (1H, m), 3.57–3.80 (3H, m), 8.90 (1H, br.s), 11.65 (1H, br.s). MS Calculated mass for C$_{10}$N$_{16}$N$_4$=192.1375 Observed mass=192.1375

EXAMPLES 29 and 30

(±) 5-(Tetrazol-2-yl)- and (±) 5-(tetrazol-1-yl)-1-azabicyclo[3.2.1]octane oxalate salts (E29) and (E30)

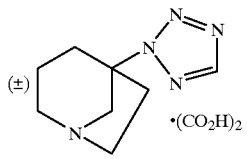

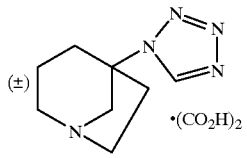

(±) 5-Bromo-1-azabicyclo[3.2.1]octane (D23, 1.1 g, 5.8 mmol) was treated with sodium tetrazole (D16, 1.85 g, 20.1 mmol) in dry DMF (50 ml) at reflux for 5 h. The reaction mixture was concentrated in vacuo and the residue partitioned between saturated aqueous potassium carbonate solution (50 ml) and chloroform (4×75 ml). The combined organic extracts were dried and evaporated to give an oil which was chromatographed on silica using 10% methanol/chloroform as eluant to give, in order of elution, the 2-substituted tetrazole as a low-melting solid (0.59 g) and the 1-substituted tetrazole as a white solid (0.11 g) m.p. 112–114° C. The 2-substituted tetrazole was converted to the oxalate salt and recrystallised from water/methanol/acetone to give the title compound (E29) as a white solid (0.88 g, 57%) m.p. 205–207° C. The 1-substituted tetrazole was likewise converted to the oxalate salt and recrystallised from methanol to give the title compound (E30) as a white solid (0.15 g, 10%) m.p. 184–186° C. (decomp.)

(E29); $^1$H NMR (d$_6$DMSO) δ: 1.96 (1H, m), 2.18–2.33 (3H, m), 2.60 (2H, m), 3.24 (2H, m), 3.44 (1H, m), 3.57–3.94 (3H, m), 9.08 (1H, s). $^{13}$C NMR (d$_6$DMSO) δ: 17.32, 32.37, 34.83, 49.18, 51.27, 58.75, 67.71, 153.30; Analysis: C$_8$H$_{13}$N$_5$.C$_2$H$_2$O$_4$ requires C: 44.61; H: 5.62; N: 26.01; found C: 44.37; H: 5.60; N: 25.95

(E30) $^1$H NMR (d$_6$DMSO) δ: 1.96 (1H, m), 2.05–2.28 (3H, m), 2.45–2.67 (2H, m), 3.23 (2H, m), 3.44 (1H, m), 3.55–3.83 (3H, m), 9.67 (1H, s). $^{13}$C NMR (d$_6$DMSO) δ: 17.24, 32.63, 34.92, 49.07, 51.28, 58.79, 63.79, 142.68; Analysis; C$_8$H$_{13}$N$_5$.C$_2$H$_2$O$_4$ requires C: 44.61; H: 5.62; N: 26.01; found C: 44.43; H: 5.63; N: 25.78

EXAMPLES 31 and 32

(±) 5-(5-Methyltetrazol-2-yl)- and (±) 5-(5-methyltetrazol-1-yl)-1-azabicyclo[3.2.1]octane oxalate salts (E31) and (E32)

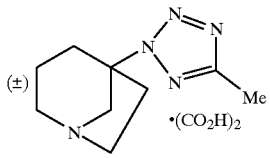
(E31)

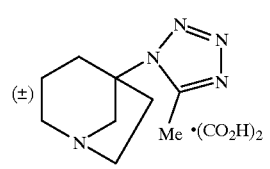
(E32)

(±) 5-Bromo-1-azabicyclo[3.2.1]octane (D23, 0.5 g, 2.63 mmol) was treated with the sodium salt of 5-methyltetrazole (D17, 1.27 g, 11.98 mmol) in dry DMF (25 ml) at reflux for 2.75 h. The reaction was worked-up as in the method of Example 29 and 30 and chromatographed on silica using 9% methanol/chloroform as eluant to give, in order of elution, the 2-substituted methyltetrazole as an oil (0.24 g, 47%) and the 1-substituted methyltetrazole as a white solid (0.20 g, 39%) m.p. 97–100° C. The 2-substituted methyltetrazole was converted to the oxalate salt and recrystallised from methanol/acetone to give the title compound (E31) as a white crystalline solid m.p. 145–147° C. The 1-substituted methyltetrazole was similarly converted to the oxalate salt and recrystallised from methanol/acetone to give the title compound (E32) as a white solid m.p. 205–208° C. (decomp.).

(E31) $^1$H NMR (d$_6$DMSO) δ: 1.97 (1H, m), 2.10–2.28 (3H, m), 2.48 (3H, s), 2.48–2.68 (2H, m), 3.26 (2H, m), 3.44 (1H, m), 3.66 (1H, m), 3.73 and 3.85 (2H, ABq, J=11 Hz). $^{13}$C NMR (d$_6$DMSO) δ: 10.46, 17.25, 32.29, 34.67, 49.10, 51.21, 58.65, 67.40, 162.39. Analysis: C$_9$H$_{15}$N$_5$.C$_2$H$_2$O$_4$ requires C: 46.64; H: 5.62; N: 24.72; found C: 46.50; H: 6.04; N: 24.40.

(E32) $^1$H NMR (d$_6$DMSO) δ: 1.84–2.20 (4H, m), 2.50 (1H, m), 2.61 (3H, s), 2.77 (1H, m), 3.25 (2H, m), 3.43 (1H, m), 3.58 (1H, m), 3.87 (2H, m). $^{13}$C NMR (d$_6$DMSO) δ: 9.70, 17.41, 31.39, 34.60, 49.20, 51.04, 58.81, 64.02, 151.71. Analysis: C$_9$H$_{15}$N$_5$.C$_2$H$_2$O$_4$ requires C: 46.64; H: 5.62; N: 24.72; found C: 46.39; H: 6.06; N: 24.39.

EXAMPLES 33 and 34

(±) 5-(5-Aminotetrazol-2-yl)- and (±) 5-(5-aminotetrazol-1-yl)-1-azabicyclo[3.2.1]octane (E30) and (E31)

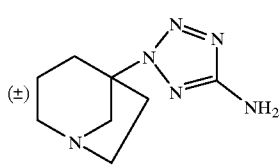
(E33)

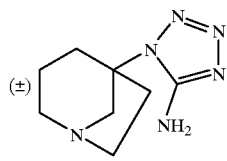
(E34)

(±) 5-Bromo-1-azabicyclo[3.2.1]octane (D23, 0.5 g, 2.63 mmol) was treated with the sodium salt of 5-aminotetrazole (D15, 0.56 g, 5.23 mmol) in dry DMF (15 ml) at reflux for 1 h. The reaction was worked-up as in the method of Example 29 and 30 and chromatographed on silica using a graded eluant of 12–20% methanol/chloroform. This gave, in order of elution, the 2-substituted aminotetrazole (E33), which was recrystallised from methanol/ether to give a white solid (0.13 g, 24%) m.p. 173–175° C., and the 1-substituted aminotetrazole (E34) (0.07 g, 14%). m.p. 220–223° C. (decomp.).

(E33) $^1$H NMR (CD$_3$OD) δ: 1.77 (1H, m), 1.94–2.26 (1H, m), 2.22 (2H, m), 2.41 (2H, t, J=9 Hz), 2.86 (2H, m), 3.06 (1H, m), 3.18–3.36 (3H, m), 4.90 (2H, br). $^{13}$C NMR (CD$_3$OD) δ: 21.33, 36.66, 37.88, 52.03, 55.04, 63.78, 70.28, 168.80. λmax 247 nm (ε3570, EtOH); M.S. Calculated mass for C$_8$H$_{14}$N$_6$=194.1280 Observed mass=194.1278

(E34) $^1$H NMR (CD$_3$OD) δ: 1.71 (1H, m), 1.96 (2H, m), 2.07–2.22 (2H, m), 2.70 (1H, m), 2.89 (2H, m), 3.06 (1H, m), 3.18–3.37 (2H, m), 3.46 (1H, m), 4.80 (2H, br). $^{13}$C NMR (CD$_3$OD) δ: 20.80, 34.45, 35.71, 51.73, 54.39, 63.21, 64.77, 156.50; λmax 219 nm (ε3530, EtOH); M.S. Calculated mass for C$_8$H$_{14}$N$_6$=194.1280; Observed mass= 194.1282

EXAMPLE 35

(±) 3-(1,2,3-triazol-1-yl)-1-azabicyclo[2.2.2]octane (E35)

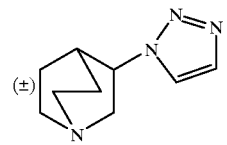

(±) 3-Azido-1-azabicyclo[2.2.2]octane oxalate salt (D25) (200 mg, 0.0083 mole) in acetone (20 ml) was treated with acetylene dicarboxylic acid (500 mg, 0.0044 mole) and concentrated in vacuo to produce a homogenous gum. Xylene (20 ml) was added and the solution heated to reflux for 10 min when the suspension rapidly darkened and evolved carbon dioxide. The xylene was then removed in vacuo and the residue partitioned between chloroform and saturated aqueous potassium carbonate solution. The organic phase was separated, dried over sodium sulphate and concentrated in vacuo to a gum. Chromatography on alumina in a gradient of 5–30% methanol in ethyl acetate afforded the title compound (E35) which crystallised from 40–60° petrol as needles m.p. 62–65° C. (60 mg, 0.0034 moles, 40%).

$^1$H NMR (270 MHz, CDCl$_3$) δ: 1.3–1.48 (1H, m), 1.48–1.63 (1H, m), 1.63–1.82 (2H, m), 2.1–2.25 (1H, m), 2.75–2.95 (3H, m), 2.95–3.15 (1H, m), 3.33–3.48 (1H, m), 3.53–3.68 (1H, m), 4.5–4.65 (1H, m), 7.55 (1H, s), 7.68 (1H, s). $^{13}$C NMR (CDCl$_3$, 68 MHz) δ: 19.9 and 25.9 (C-5,7), 28.1 (C-4), 46.9, 47.2 and 52.7 (C-2,6,8), 58.1 (C-3), 122.7 and 133.7 (C-4' and C-5')

EXAMPLE 36 and 37

(±) 5-(3-Amino-1,2,4-triazol-1-yl)- and (±) 5-(5-amino-1,2,4-triazol-1-yl)-1-azabicyclo[3.2.1]octanes (E36) and (E37)

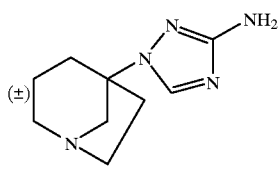
(E36)

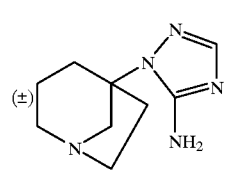
(E37)

(±) 5-Bromo-1-azabicyclo[3.2.1]octane (D23, 2 g, 10.5 mmol) was treated with the sodium salt of 3-amino-1,2,4-triazole (D20, 2.23 g, 21.0 mmol) in dry DMF for 1 h. The reaction was worked-up as in the method of Example 29 and 30 and chromatographed on basic alumina using a graded eluant of 0–2% methanol/chloroform to give, in order of elution, the 3-aminotriazole (E36), which was recrystallised from methanol/ether to give a white solid (0.29 g, 14%) m.p. 172–174° C., and the 5-aminotriazole (E37) as a white solid (0.28 g, 14%) m.p. 190–194° C.

E36 $^1$H NMR (CDCl$_3$) δ: 1.72 (1H,m), 1.90 (1H,m), 2.09 (2H,m), 2.22 (2H,m), 2.74–3.05 (4H,m), 3.27–3.36 (2H,m), 4.20 (2H,br.s), 7.68 (1H,s); $^{13}$C NMR (CDCl$_3$) δ: 20.40, 35.82, 37.04, 51.25, 54.19, 63.50, 64.53, 139.69, 163.19.

E37 1H NMR (CDCl$_3$/DMSO) δ: 1.64 (1H,m), 1.87 (2H,m), 2.10 (2H,m), 2.51 (1H,m), 2.75–3.20 (4H,m), 3.18–3.36 (2H,m), 5.27 (2H,br.s), 7.32 (1H,m).

$^{13}$C NMR (CDCl$_3$/DMSO) δ: 19.51, 33.98, 34.34, 50.61, 53.03, 62.64, 77.24, 146.85, 153.38.

EXAMPLE 38 and 39

(±) 3-(3-Amino-1,2,4-triazol-1-yl)-1-azabicyclo-[2.2.2]octane (E38) and (±) 3-(5-amino-1,2,4-triazol-1-yl)-1-azabicyclo[2.2.2]octane dihydrochloride salt (E39)

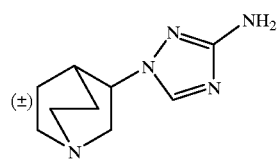
(E38)

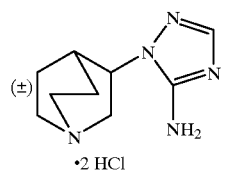
(E39)

(±) 3-Methanesulphonyloxy-1-azabicyclo[2.2.2]octane (D8) (5.0 g, 0.024 mol) and the sodium salt of 3-amino-1,2,4-triazole (D20) (7.0 g, 0.066 mol) in dry DMF was heated at reflux for 1.5 h, and the reaction carried out as in Example 10. The mixture was purified by column chromatography using basic alumina eluting with chloroform/methanol (0–2%), to give, in order of elution, E38 which was recrystallised from EtOAc/40–60 petrol to give a white solid (150 mg, 3.2%) m.p. 144–146° C. and E39 which was crystallised from methanol/ether as the dihydrochloride salt (110 mg, 1.7%) m.p. 257–259° C.

E38 $^1$H NMR (CDCl$_3$) δ: 1.43 (1H,m), 1.78 (1H, complex m), 2.05 (2H,m), 2.18 (1H,m), 2.89 (3H,m), 3.05 (1H,m), 4.08 (2H,m,NH$_2$), 4.2 (1H,m,CH-azole), 7.73 (1H,s,azole-H).

$^{13}$C NMR (CDCl$_3$) 20.2 (CH$_2$), 26.8 (CH$_2$), 27.5 (CH), 46.9 (CH$_2$), 47.42 (CH$_2$), 52.4 (CH$_2$), 56.8 (CH), 141.9 (azole-CH), 163.1 (quat-C).

MS C$_9$H$_{15}$N$_5$ requires 193.1327 found: 193.1331.

E39 $^1$H NMR (d$_6$DMSO): 1.89 (4H,m), 2.31 (1H,s), 3.25 (4H,m), 3.55 (1H,dd), 3.73 (1H,dt), 5.03 (1H,m), 8.40 (1H,S, azole-H); $^{13}$C NMR (d$_6$DMSO): 17.0 (CH$_2$), 20.8 (CH$_2$), 24.5 (CH), 44.8 (CH$_2$), 45.5 (CH$_2$), 48.1 (CH$_2$), 50.6 (CH), 138.8 (CH-azole), 149.5 (quat C azole).

MS C$_9$H$_{15}$N$_5$ requires 193.1327, found 193.1327.

EXAMPLE 40

(±) 3-[5-Bromotetrazol-2-yl]-1-azabicyclo[2.2.2]octane oxalate salt (E40)

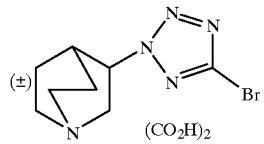
(E40)

Tertiary butyllithium in pentane (7 ml of a 1.7 molar solution, 0.0104 mole) in dry pentane (25 ml) at −65° C. under nitrogen was treated with 3-(tetrazol-2-yl)-1-azabicyclo[2.2.2]octane (the free base of E15) (1.0 g; 5.2 mmole) in a dry pentane (50 ml)/dry THF (10 ml) mixture, maintaining an internal temperature of −65° C. Stirring was continued for 10 minutes. Bromine (2 eq, 1.66 g, 10.4 mmole) in dry pentane (5 ml) was then added dropwise. The mixture was then immediately quenched with glacial acetic acid (2 eq, 0.62 ml, 10.4 mmole), then partitoned between aqueous potassium carbonate (20 ml) and chloroform (5×20 ml). The combined organic extracts were dried (Na$_2$SO$_4$) and concentrated in vacuo, to afford an oil which was chromatographed on neutral alumina eluting with ethyl acetate, to afford in order of elution the title compound (free base) (220 mg as an oil) and unreacted starting material. The free base was converted to the oxalate salt and recrystallised from acetone/ether to give the title compound (E40) as a white crystalline solid (0.113 g, 0.00032 mole, 6%) m.p. 165° C. (decomp.).

$^1$H NMR (DMSO) δ: 1.58–1.78 (2H, m), 1.90–2.03 (2H, m), 2.52–2.61 (1H, m), 3.12–3.25 (4H, m), 3.78–3.84 (2H, d, J=5.5 Hz), 5.39–5.50 (1H, m).

$^{13}$C NMR (DMSO) δ: 18.4 and 22.4 (C-5, 8), 27.4 (C-4), 47.3, 47.6 and 50.8 (C-2,6,7), 60.3 (C-3), 144.1 (C-5'), 166.7 ((CO$_2$H)$_2$)

EXAMPLE 41

(±) exo-3-(5-Bromotetrazol-2-yl)-1-azabicyclo [2.2.1]heptane oxalate salt (E41)

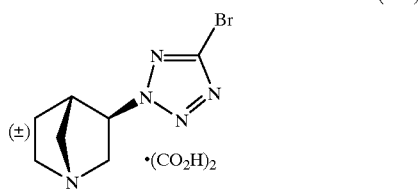

(E41)

(±) exo-3-(Tetrazol-2-yl)-1-azabicyclo[2.2.1]heptane (the free base of E19) (0.38 g, 2.3 mmol) in dry THF (20 ml) was added dropwise under nitrogen to a stirred solution of tertiary butyllithium (2.55 ml of a 1.7M solution in pentane, 4.3 mmol, 2 eqs) in dry pentane (10 ml) at −65° C. under nitrogen maintaining the temperature below −40° C. throughout the addition. The yellow precipitate was stirred at −65° C. for 5 minutes. Bromine (0.22 ml, 4.3 mmol, 2 eq) in pentane (10 ml)/THF (10 ml) was added dropwise, immediately followed by quenching with glacial acetic acid (0.26 ml, 2 eq) and the mixture allowed to warm to 0° C. Saturated aqueous potassium carbonate (30 ml) was added, the solution extracted with CHCl$_3$, the organic extracts dried (Na$_2$SO$_4$), filtered and evaporated to dryness under reduced pressure to yield a yellow oil. This was purified by column chromatography (b Al$_2$O$_3$, EtOAc/1–5% MeOH) to yield the required compound (0.37 g, 67%) which was crystallised from methanol/diethyl ether as oxalate salt to afford the title compound (E41) m.p. 144–146° C.

$^1$H NMR (d$_6$ DMSO); 1.83 (1H, m), 2.00 (1H, m), 3.04 (2H, d), 3.23 (3H, complex m), 3.67 (2H, m), 5.30 (1H, m) $^{13}$C NMR (d$_6$ DMSO); 24.7 (CH$_2$), 41.9 (CH), 51.7 (CH$_2$), 57.1 (CH$_2$), 58.2 (CH$_2$), 64.1 (CH), 142.3 (azole C-Br), 163.6 (oxalate). Analysis: C$_7$H$_{10}$N$_5$B$_r$.C$_2$H$_2$O$_4$; requires: C 32.35; H 3.62; N 20.96%; found: C 32.36; H 3.63; N 20.65%

EXAMPLE 42

(±) exo-3-(5-Chlorotetrazol-2-yl)-1-azabicyclo [2.2.1]heptane oxalate salt (E42)

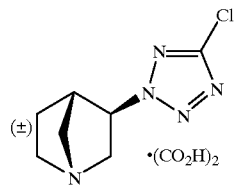

(E42)

This synthesis was carried out as for Example 41 but using a solution of chlorine gas (2 eqs) in CCl$_4$ instead of bromine to quench the tetrazole anion. The resulting crude oil was purified by column chromatography (b.Al$_2$O$_3$. EtOAc/1–5% MeOH) to yield the chlorotetrazole (0.30 g, 65%) which was crystallised from methanol/diethyl ether as an oxalate salt to afford the title compound (E42), m.p. 125–128° C.

$^1$H NMR (d$_6$ DMSO); 1.73 (1H, m), 2.00 (1H, m), 3.05 (2H, m), 3.21 (1H, m), 3.31 (2H, t), 3.71 (2H, complex m), 5.28 (1H, m). $^{13}$C NMR (d$_6$ DMSO); 24.7 (CH$_2$), 41.6 (CH), 51.6 (CH$_2$), 57.0 (CH$_2$), 58.3 (CH$_2$), 64.3 (CH), 154.3 (azole C-Cl), 163.7 (oxalate). M.S. C$_7$H10N$_5$Cl requires 199.0624; found 199.0631; Analysis: C$_7$H$_{10}$N$_5$Cl.C$_2$H$_2$O$_4$; requires C, 37.36; H, 4.18; N, 24.22%; found C, 37.26; H, 4.22; N, 24.03%

EXAMPLE 43

(±) exo-3-(5-Iodotetrazol-2-yl)-1-azabicyclo[2.2.1] heptane oxalate salt (E43)

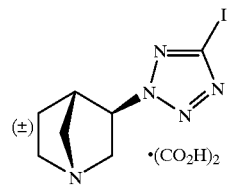

(E43)

This synthesis was carried out as for Example 41 but using iodine (0.93 g, 2 eq) in THF (20 ml) instead of bromine to quench the tetrazole anion. The resulting crude oil was purified by column chromatography (b.Al$_2$O$_3$, EtOAc/MeOH 1–5%) to yield the iodotetrazole (0.281 g, 42%) which was crystallised from methanol/diethyl ether as an oxalate salt to afford the title compound (E43), m.p. 158–161° C.

$^1$H NMR (d$_6$ DMSO); 1.83 (1H, m), 2.08 (1H, m), 3.13 (2H, d), 3.33 (3H, complex m), 3.78 (2H, m), 5.38 (1H, m). $^{13}$C NMR (d$_6$ DMSO); 24.8 (CH$_2$), 41.9 (CH), 51.7 (CH$_2$), 57.1 (CH$_2$), 58.6 (CH$_2$), 63.6 (CH) 115.5 (azole C-I), 163. 7 (oxalate).

EXAMPLE 44

(±) 3-(5-Chlorotetrazol-2-yl)-1-azabicyclo[2.2.2]
octane oxalate salt (E44)

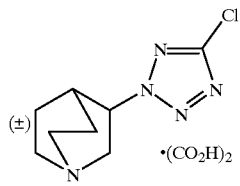

Tertiary butyllithium (a solution of 1.7 molar in pentane) (7 ml; 10.4 mmole, 2 eq) in dry hexane (25 ml) at −65° C. under nitrogen was treated with 3-(tetrazol-2-yl)-1-azabicyclo[2.2.2]octane (the free base of E15) (1 g; 5.2 mmole) in dry tetrahydrofuran (25 ml) maintaining an internal temperature of less than −50° C. throughout the addition. The resulting yellow solution was stirred at −60° C. for 10 minutes before treatment with chlorine (2 eq; 0.74 g; 10.4 mmole) in dry hexane (20 ml) at −60° C. over a period of 5 minutes. After complete addition the reaction mixture was quenched with glacial acetic acid (2 eq), then partitioned between aqueous potassium carbonate and chloroform. The organic extracts were dried over sodium sulphate, then concentrated under reduced pressure to afford an orange oil. Column chromatography on silica in a gradient of 2–10% methanol in chloroform, afforded the title compound and a slower running impurity. Further chromatography on neutral alumina in neat ethyl acetate afforded the pure title compound as an orange oil which was crystallised from methanol/diethyl ether as an oxalate salt (E44) (0.139g; 10%), m.p. (dec) 127–129° C.

$^1$H NMR (CD$_3$OD) δ: 1.80–2.04 (2H, m), 2.18–2.28 (2H, m, 5-C, 7-C), 2.70–2.78 (H, m, 4-C) 3.39–3.61 (4H, m, 6-C, 8-C), 3.95–4.28 (2H, m, 2-C), 5.52–5.62 (H, m, 3-C).

$^{13}$C NMR (CD$_3$OD) δ: 17.32, 21.43 (both CH$_2$, 5, 7), 25.44 (CH, 4), 45.28 (CH$_2$, 6), 45.62 (CH$_2$, 8), 49.78 (CH$_2$, 2), 59.16 (CH, 3), 154.34 (azole C-Cl), 163.87 (oxalate).

EXAMPLE 45

(±) 3-(5-Iodotetrazol-2-yl)-1-azabicyclo[2.2.2]
octane (E45)

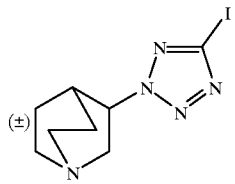

Tertiary buthyllithium (1.7 molar solution in pentane) (2 eq; 8.6 ml; 12.8 mmole) in dry hexane (25 ml) under nitrogen at −65° C. was treated with 3-(tetrazol-2-yl)-1-azabicyclo[2.2.2]octane (the free base of E15) (1.254 g; 6.4 mmole) in dry tetrahydrofuran (50 ml) maintaining an internal temperature of −60 to −65° C. thoughout the addition. The resulting yellow solution was stirred at −60° C. for 10 minutes before treatment with iodine (2 eq; 3.25 g; 12.8 mmole) in dry hexane (10 ml) over 5 minutes at −60° C. The reaction mixture was immediately quenched with glacial acetic acid (2 eq), then partitioned between aqueous potassium carbonate and chloroform. The combined chloroform extracts were dried over sodium sulphate, and washed with sodium metabisulphite to remove the free iodine. The solution was concentrated under reduced pressure to afford a crude yellow gum which was purified by column chromatography on silica gel in a gradient of 2–7% methanol in chloroform. Elution with 6% methanol in chloroform gave the major fraction as a gum which was triturated with ether in methanol to afford the title compound (E45) (0.028 g, 1.5%), m.p. 160–165° C. (Dec).

$^1$H NMR (CD$_3$OD) δ: 1.63–1.85 (2H, m), 2.05–2.12 (2H, m, 5-C and 7-C), 2.58–2.62 (H, m, 4C), 3.20–3.39 (4H, m, 6-C and 8-C), 3.78–3.86 (1H, m, 2-C), 3.95–4.02 (1H, m, 2-C), 5.39–5.45 (1H, m, 3-C). $^{13}$C NMR (CD$_3$OD) δ: 19.2, 23.8 (both CH$_2$, 7-C and 5-C), 27.9 (CH$_2$, 4-C), 47.5, 47.9, 51.5 (all CH$_2$, 2-C, 6-C, 8-C), 61.0 (CH, 3-C), 114.4 (azole C-I)

EXAMPLE 46

(±) 3-(5-Cyanotetrazol-2-yl)-1-azabicyclo[2.2.2]
octane oxalate salt (E46)

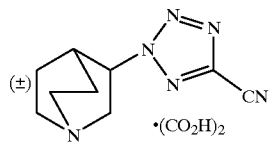

A 1.7 molar solution of t-butyllithium in pentane (1.2 eq; 4.54 ml; 6.7 mmol) was diluted with dry hexane (10 ml) under nitrogen and cooled to −65° C. The cold solution was treated with 3-(tetrazol-2-yl)-1-azabicyclo[2.2.2]octane (free base of E15) (1g, 5.6mm) in dry tetrahydrofuran (20 ml) dropwise, maintaining an internal temperature below −50° C. The resulting yellow precipitate was then treated with N-methylformanilide (1.2 eq; 0.9 g, 6.7 mmol) in dry tetrahydrofuran (10 ml), dropwise maintaining an internal temperature of below −50° C. Stirring at this temperature was continued for 30 minutes. The cold reaction mixture was then poured into dilute hydrochloric acid (25 ml) and stirred for 10 minutes. The reaction mixture was basified with aqueous potassium carbonate and extracted into chloroform. The combined organic extracts were (Na$_2$SO$_4$) and evaporated to dryness under reduced pressure. The resulting crude aldehyde was dissolved in methanol (10 ml) and treated with hydroxylamine hydrochloride (1.1 eq; 0.43 g, 6.14 mmol) at room temperature. Stirring was continued for 5 hours. The mixture was concentrated in vacuo to a gum which was treated with saturated aqueous potassium carbonate, and the aldoxime extracted into chloroform. The combined organic extracts were dried (Na$_2$SO$_4$) and evaporated to dryness under reduced pressure to a gum. The resulting crude aldoxime was dissolved in acetic anhydride (20 ml) and heated at 80° C. for 1 hour. After cooling acetic anhydride was removed in vacuo and the resulting viscous oil was treated with aqueous potassium carbonate and extracted with chloroform. Combined organic extracts were dried (Na$_2$SO$_4$) and evaporated to dryness under reduced pressure to a gum. Column chromatography (neutral alumina, eluting with 1% methanol in ethyl acetate) afforded a yellow oil which was crystallised as an oxalate salt from acetone/ether, to afford the title compound (E46) (0.088 g, 5.4%) as colourless needles. m.p. 175° C. (Dec).

¹H NMR (CD₃OD) δ: 1.66–1.93 and 2.08–2.20 each (2H, m, 5-CH₂ and 7-CH₂), 2.64–2.72 (1H, m, 4-H), 3.22–3.45 (4H, m, 6-CH₂ and 8-CH₂), 3.85–4.09 (2H, m, 2-CH₂), 5.55–5.64 (1H, m, 3-CH).

¹³C NMR (CD₃OD) δ: 18.86, 23.35 (C5 and C7), 27.74 (C4), 47.25 (C6), 47.63 (C8), 51.35 (C2), 61.76 (C3), 110.19 (nitrile C), 143.56 (C5'), 167.74 (oxalate).

EXAMPLE 47

(±) 3-(3-Bromo-1,2,4-triazol-1-yl)-1-azabicyclo[2.2.2]-octane oxalate salt (E47)

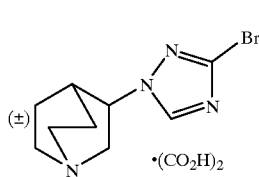

(±) 3-(3-Amino-1,2,4-triazol-1-yl)-1-azabicyclo[2.2.2]-octane (E38) (100 mg, 0.52 mmol) in 30% hydrobromic acid (25 ml) was cooled to below 0° C. on a MeOH/ice bath, and stirred while a solution of sodium nitrite (40 mg, 0.58 mmol) in water (2 ml) was slowly added and the mixture stirred for 5 minutes. The cold orange solution was added dropwise to a cold solution of cuprous bromide (81 mg, 0.58 mmol) and allowed to stand for 5 min. The dark blue/black solution was heated to 80° C. until nitrogen evolution ceased and then allowed to cool. Saturated aqueous potassium carbonate solution was added and the aqueous phase extracted several times with ethyl acetate. The organic extracts were dried (Na₂SO₄), filtered and evaporated to dryness under reduced pressure to yield an orange oil which was purified by column chromatography (basic Al₂O₃, EtOAc/MeOH 1–5%), to yield a colourless oil (40 mg, 29%) which was crystallised as an oxalate salt from methanol/diethyl ether to give a white crystalline solid. m.p. 128–130° C. ¹H NMR (d₆ DMSO) δ: 1.74 (2H, m), 1.93 (2H, m), 2.40 (1H, m), 3.19 (3H, m), 3.31 (1H, m), 3.64 (1H, dd), 3.75 (1H, t), 4.96 (1H, m), 8.76 (1H, s, azole-H); ¹³C NMR (d₆ DMSO) δ: 17.4 (CH₂), 21.9 (CH₂), 26.1 (CH), 45.2 (CH₂), 45.8 (CH₂), 49.4 (CH₂), 54.2 (CH), 138.5 (quat-C, azole), 146.2 (CH-azole), 164.2 (oxalate). MS: 256.0326; C₉H₁₃N₄Br requires 256.0323

EXAMPLE 48

(±) 3-(3-Chloro-1,2,4-triazol-1-yl)-1-azabicyclo[2.2.2] octane oxalate salt (E48)

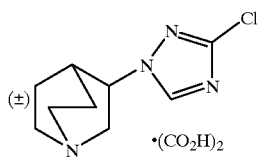

(±) 3-(3-Amino-1,2,4-triazol-1-yl)-1-azabicyclo[2.2.2]-octane (E38) (239 mg, 1.24 mmol) was converted to the 3-chlorotriazole according to the method of Example 47, using concentrated hydrochloric acid (30 ml), sodium nitrite (184 mg, 2.6 mmol) and cuprous chloride (264 mg, 2.6 mmol). The resulting oil was purified by column chromatography (basic Al₂O₃, EtOAc/MeOH (1–5%)) and the product (110 mg, 41%) crystallised from methanol/diethyl ether as an oxalate salt. m.p. 119–121° C.

¹H NMR (d₆ DMSO) δ: ¹³C NMR (d₆ DMSO) δ: MS: Found 212.0829; C₉H₁₃N₄Cl requires 212.0828; Analysis:- C₉H₁₃N₄Cl.C₂H₂O₄; found: C: 43.48; H: 4.78; N: 18.21%; required: C: 43.64; H: 5.00; N: 18.51%

EXAMPLE 49

(±) 5-(5-Chlorotetrazol-2-yl)-1-azabicyclo[3.2.1]octane oxalate salt (E49)

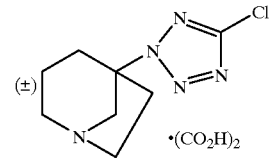

5-(Tetrazol-2-yl)-1-azabicyclo[3.2.1]octane (the free base of E29) (0.25 g, 1.40 mmol) was converted to the 5-chlorotetrazole according to the method of Example 42. Chromatography on silica using 3% methanol/chloroform afforded the 5-chlorotetrazole as an off-white solid (0.15 g, 50%) m.p. 72–74° C. This material was converted to an oxalate salt and recrystallised from methanol/acetone to afford the title compound (E49) as a white crystalline solid, m.p. 189° C. (decomp.).

¹H NMR (d₆ DMSO, 270 MHz) δ: 1.87–2.34 (4H, m), 2.60 (2H, m), 3.23 (2H, m), 3.53 (1H, m), 3.52–3.74 (2H, m), 3.81 (1H, m) ¹³C NMR (d₆ DMSO, 270 MHz) δ: 17.40, 32.20, 34.48, 49.20, 51.31, 58.74, 69.10, 154.30; MS Calculated mass for C₈H₁₂N₅Cl=213.0781; Observed mass=213.0782

EXAMPLE 50

(±) 5-(5-Bromotetrazol-2-yl)-1-azabicyclo[3.2.1]octane (E50)

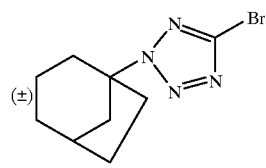

5-(Tetrazol-2-yl)-1-azabicyclo[3.2.1]octane (the free base of E29) (0.2 g, 1.12 mmol) was converted to the 5-bromotetrazole according to the method of Example 40. Chromatography on silica using 4% methanol/chloroform afforded the title compound (E50) as a white crystalline solid (0.16 g, 56%) m.p. 108–110° C.

¹H NMR (CDCl₃, 270 MHz) δ: 1.72–2.05 (2H, m), 2.28 (2H, m), 2.46 (2H, m), 2.80–3.08 (3H, m), 3.22–3.41 (3H, m). ¹³C NMR (CDCl₃) δ: 20.74, 36.28, 37.10, 51.53, 54.30, 63.92, 70.81, 142.68; M.S. Calculated mass for C₈H₁₂N₅Br=257.0275, 259.0255; Observed mass 257.0280, 259.0256 Analysis: C₈H₁₂N₅Br; requires C: 37.23, H: 4.69, N: 27.13%; found C: 37.69, H: 4.57, N: 27.06%

EXAMPLE 51

4-(1,2,4-Triazol-1-yl)-1-azabicyclo[2.2.1]heptane oxalate salt (E51)

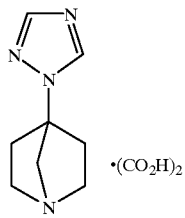

(E51)

A stirred solution of 1-benzyl-4-hydroxymethyl-4-(1,2,4-triazol-1-yl)piperidine (D29, 320 mg, 0.0018 mol) in dry pyridine (5 ml) at 0° C. was treated with 4-toluenesulphonyl chloride (225 mg, 0.00118 mol) and the resulting red solution kept at 5° C. for 20 h, followed by room temperature for 3 days. The solution was concentrated in vacuo and the residue treated with saturated potassium carbonate solution and extracted with chloroform (3×30 ml). The combined extracts were dried ($Na_2SO_4$) and concentrated in vacuo to leave an orange oil, which was treated with toluene (30 ml) and heated under reflux for 2 h. The toluene solution was decanted off and the orange gum remaining was dissolved in ethanol (40 ml) together with glacial acetic acid (1 ml) and hydrogenated over 10% palladium/charcoal (200 mg) at atmospheric pressure and 40° C. until reduction was complete (1 h). The catalyst was removed by filtration through Kieselguhr and the filtrate concentrated in vacuo. The residue was basified with saturated potassium carbonate solution and extracted with chloroform (3×30 ml). The combined extracts were dried ($Na_2SO_4$) and concentrated in vacuo to leave a yellow oil, which was filtered through a plug of basic alumina eluting with ethyl acetate to give a colourless oil, which crystallised on standing. This was converted to an oxalate salt and crystallised from methanol/ether to afford the title compound (E51) as a white solid (42 mg, 14%) m.p. 142–144° C.

$^1$H NMR (d$_6$ DMSO, 250 MHz) δ: 2.20–2.50 (4H, m), 3.33–3.46 (2H, m), 3.48–3.65 (4H, m), 8.1 (1H, s), 8.77 (1H, s). $^{13}$C NMR (d$_6$ DMSO, 67.8 MHz) δ: 32.33, 52.67, 59.43, 66.39, 143.61, 151.77, 164.05 (COOH)$_2$. Required C: 47.24 H: 5.51 N: 22.05; Found C: 47.03 H: 5.57 N: 22.01

EXAMPLE 52

(±) exo-3-(3-Amino-1,2,4-triazol-1-yl)-1-azabicyclo-[2.2.1]heptane (E52) and (±) exo-3-(5-amino-1,2,4-triazol-1-yl)-1-azabicyclo[2.2.1]heptane (E55)

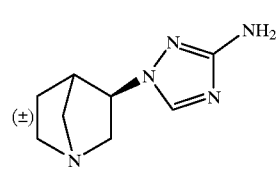

(E52)

endo-3-(Methanesulphonyloxy)-1-azabicyclo[2.2.1]heptane (D10) (4.2 g; 0.035 mole) was dissolved in dry dimethylformamide (100 ml), and treated with the sodium salt of 3-amino-1,2,4-triazole (D20) (1.5 eq; 5.3 g; 0.05 mole). The mixture was heated at reflux for 1 hour, then allowed to cool to room temperature. Dimethylformamide was removed in vacuo and the resulting residue treated with aqueous potassium carbonate and extracted exhaustively into chloroform. Combined organic extracts were dried ($Na_2SO_4$), then concentrated in vacuo to leave a crude orange oil. This was purified by column chromatography (basic alumina, 10–20% methanol/chloroform) to yield separately the less polar title compound (E52) (0.633 g) and the more polar compound (E55) (0.604 g). Both were crystallised from acetone to give white crystalline solids (total yield 1.237 g, 20%).

E52 m.p. 150–152° C.; $^1$H NMR (270 MHz, CDCl$_3$) δ: 1.2 (1H, m), 1.74 (1H, m), 2.47 (2H, m), 2.87 (2H, complex m), 3.08 (3H, complex m), 3.92 (1H, m), 4.3 (2H, bs, NH$_2$), 7.72 (1H, s, azole-H).

E55 m.p. 171° C. (decomp). $^1$H NMR (270 MHz, CD$_3$OD) δ: 1.49 (1H, m), 1.75 (1H, m), 2.42 (1H, d), 2.55 (1H, m), 2.69 (1H, d), 2.82 (1H, m), 3.04 (1H, complex m), 3.20 (2H, d), 4.02 (1H, m), 7.39 (1H, s, azole-H).

EXAMPLE 53

(±) exo-3-(3-Chloro-1,2,4-triazol-1-yl)-1-azabicyclo-[2.2.1]heptane hydrochloride salt (E53)

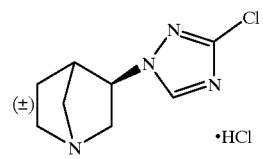

(E53)

(±) exo-3-(3-Amino-1,2,4-triazol-1-yl)-1-azabicyclo-[2.2.1]heptane (E52) (150 mg, 0.84 mmol) was converted to the 3-chlorotriazole according to the method of Example 48. The resulting oil was purified by column chromatography (basic Al$_2$O$_3$, 1–5% MeOH/EtOAc) and the product (73 mg, 44%) was crystallised from methanol/diethyl ether as the hydrochloride salt.

$^1$H NMR (270 MHz, DMSO) δ: 1.66–1.8 (1H, m, 5H), 2.0–2.16 (1H, m, 5H), 3.13–3.9 (7H, m), 4.87–5.0 (1H, m, 3H), 8.78 (1H, s, 5'H). $^{13}$C NMR (67 MHz, DMSO) δ: 24.3 (C-5), 41.5 (C-4), 51.0, 56.7 and 57.4 (C2, 6 and 7), 59.0 (C-3), 146.2 (C-5'), 151.0 (C-3').

EXAMPLE 54

(±) exo-3-(3-Bromo-1,2,4-triazol-1-yl)-1-azabicyclo-[2.2.1]heptane oxalate salt (E54)

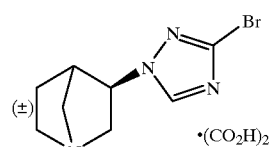

(E54)

A mixture of of (±) exo-3-(3-amino-1,2,4-triazol-1-yl)-1-azabicyclo[2.2.1]heptane (E52) and (±) exo-3-(5-amino-1,2,4-triazol-1-yl)-1-azabicyclo[2.2.1]heptane (0.15 g; 0.84 mmole) (E55) was dissolved in 49% hydrobromic acid (6 ml) at 0° C. This cold solution was treated with sodium nitrite (1.2 eq; 0.07 g; 1.0 mmole) in water (3 ml). After stirring for 5 minutes this mixture was added dropwise to a cold suspension of copper (1) bromide (1.2 eq; 0.29 g; 1.0 mmole) in water (10 ml) and the mixture stirred for a further 5 minutes. The resulting blue solution was gently heated to 80° C., and this temperature was maintained until nitrogen gas ceased to evolve. The resulting brown solution was allowed to cool to room temperature, treated carefully with anhydrous potassium carbonate, and the resulting blue solution was extracted using chloroform. Combined organic extracts were dried (Na$_2$SO$_4$) then concentrated in vacuo to give an orange oil which crystallised on standing (60 mg, 29%).

$^1$H NMR (CDCl$_3$, 270 MHz) δ: 1.2–1.33 (1H, m, 5-H), 1.7–1.85 (1H, m, 5-H), 2.42–2.58 (2H, m), 2.82–2.98 (2H, m), 2.98–3.22 (3H, m), 4.05–4.13 (1H, m, 3-H), 8.0 (1H, s, 5'H). $^{13}$C NMR (CDCl$_3$, 67 MHz) δ: 28.2 (C-5), 43.4 (C-4), 58.3, 62.0, 63.2 (C-2,6,7), 139.8 (C-3') and 143.3 (C-5').

The product was crystallised from methanol/diethyl ether as an oxalate salt to give the title compound (E54) as a low melting crystalline solid.

$^1$H NMR (CD$_3$OD, 400 MHz); (oxalate) δ: 1.75–1.85 (1H, m, 5-H), 2.08–2.20 (1H,.m, 5-H), 3.09 (1H, d), 3.35–3.45 (1H, m), 3.8–3.9 (1H, m), 4.85–4.9 (1H, m, 3-H), 8.4 (1H, s, 5-H). $^{13}$C NMR (CD$_3$OD, 100.6 MHz) (oxalate) δ: 25.8 (C-5), 43.9 (C-4), 53.4, 58.9 and 59.7 (C-2, 6 and 7), 60.6 (C-3), 140.94 (C-3') and 147.5 (C-5')

EXAMPLE 56

4-(3-Methyl-1,2,4-triazol-1-yl)-1-azabicyclo[2.2.1]-heptane oxalate salt (E56)

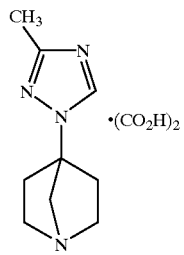

(E56)

The title compound (E56) was prepared from 1-benzyl-4-hydroxymethyl-4-(3-methyl-1,2,4-triazol-1-yl)piperidine (D31) using the method given in Example 51, as a hydroscopic white solid (6%). $^1$H NMR (CD$_3$OD, 250 MHz) δ: 2.35 (3H, s), 2.38–2.70 (4H, m), 3.50–3.70 (2H, m), 3.70–3.94 (4H, m), 8.57 (1H, s)

EXAMPLE 57

(±) exo-3-(3-Azido-1,2 4-triazol-1-yl)-1-azabicyclo-[2.2.1]heptane oxalate salt (ES7)

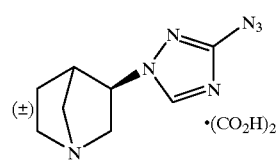

(E57)

(±) exo-3-(3-Amino-1,2,4-triazol-1-yl)-1-azabicyclo-[2.2.1]heptane (E52) (126 mg, 0.0007 moles) in 1N sulphuric acid (5 ml) was cooled to 0° C. and treated with sodium nitrite (53 mg, 0.00077 moles) in water (1 ml). The solution was allowed to stand at 0° C. for 10 min and then treated with sodium azide (91 mg, 0.0014 moles) at 0° C. The solution was allowed to warm to 25° C. over a period of 1 h. The solution was then adjusted to pH 11 with solid potassium carbonate and the aqueous solution extracted with chloroform. The organic phase was separated, dried (Na$_2$SO$_4$) and concentrated in vacuo to a gum. The gum was then chromatographed on alumina in a gradient of 2–5% methanol in ethyl acetate. The first fraction which eluted in 3% methanol in ethyl acetate was concentrated in vacuo to afford a gum (70 mg). The oxalate salt crystallised from acetone as cubes (E57) (49 mg, 0.000166 moles, 23%), m.p. 148–150° C.

$^1$H NMR (270 MHz, CD$_3$OD) δ: 1.8–2.0 (1H, m, 5-H), 2.13–2.33 (1H, m, 5H), 3.15 (1H, d, J=3 Hz), 3.25–3.4 (3H, m), 3.4–3.6 (1H, m), 3.75–3.9 (2H, m), 3.9–4.02 (1H, d, J=8 Hz), 8.43 (1H, s, 5'-H). $^{13}$C NMR (67.8 MHz, CD$_3$OD) δ: 25.9 (C-5), 43.9 (C-4), 53.3, 58.9 and 59.5 (C-2,6,7), 60.4 (C-3), 146.5 (C-5'), 159.9 (C-3') and 166.6 (CO$_2$H)$_2$.

EXAMPLE 58

(±) exo-3-(3-Nitro-1,2,4-triazol-1-yl)-1-azabicyclo-[2.2.1]heptane oxalate salt (E58)

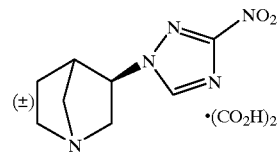

(E58)

(±) exo-3-(3-Amino-1,2,4-triazol-1-yl)-1-azabicyclo-[2.2.1]heptane (E52) (500 mg, 2.79 mmol) was dissolved in 2N sulphuric acid (10 ml) at 0° C., and this solution was added to aqueous 2N sodium nitrite (5 ml) at 0° C. The mixture was then warmed to 45° C. for 30 min, basified using saturated aqueous potassium carbonate to pH 11, and extracted with chloroform. The organic phases were dried (Na$_2$SO$_4$), evaporated to dryness under reduced pressure and purified by elution through a plug of alumina in ether. The oxalate salt was crystallised from acetone to afford the title compound (E58) (0.43 g, 1.44 mmoles, 51%) m.p. 151–153° C.

$^1$H NMR (CD$_3$OD, 250 MHz) δ: 1.9–2.05 (1H, m, 5-H), 2.2–2.4 (1H, m, 5-H), 3.27–3.63 (4H, m), 3.9–4.0 (3H, m), 5.13–5.24 (1H, m, 3H), 8.8 (1H, s, 5'H).

Biological Activity

Radio ligand Binding

Cerebral cortex from Hooded Lister rats (Olac, UK) is homogenised in 2.5 vols ice-cold 50mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1ml aliquots at −20° C.

Incubations (total volume 2 ml) are prepared using the above buffer with the addition of 2 mM magnesium chloride in the 3H-Oxotremorine-M (3H-OXO-M) experiments. For 3H-Quinuclidinyl Benzilate (3H-QNB), 1 ml of stored membranes is diluted to 30 ml and 0.1 ml mixed with test compound and 0.27 nM (c. 25,000 cpm) 3H-QNB (Amersham International). For 3H-OXO-M, 1 ml of membranes is diluted to 6 ml and 0.1 ml mixed with test compound and 2 nM (c. 250,000 cpm) 3H-OXO-M (New England Nuclear).

Non-specific binding of 3H-QNB is defined using 1 $\mu$M Atropine sulphate (2 $\mu$M Atropine) and of 3H-OXO-M using 10 $\mu$M Oxotremorine. Non-specific binding values typically are 5% and 25% of total binding, respectively. Incubations are carried out at 37° C. for 30 min and the samples filtered using Whatman GF/B filters. (In the 3H-OXO-M experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as $IC_{50}$ values (i.e. the concentration which inhibits binding of the ligand by 50%) for the displacement of the muscarinic agonist 3H-OXO-M and the muscarinic antagonist 3H-QNB. The ratio $IC_{50}$(3H-QNB)/$IC_{50}$(3H-OXO-M) gives an indication of the agonist character of the compound. Agonists typically exhibit a large ratio; antagonists typically exhibit a ratio near to unity.

The results are shown in Table 1:

TABLE 1

| Compound | [$^3$H]-oxo-M $IC_{50}$ (nm) | [$^3$H]-QNB $IC_{50}$ (nm) |
| --- | --- | --- |
| E1 | 369 | 5,000 |
| E2 | 1249 | 35,000 |
| E5 | 651 | 30,300 |
| E6 | 67.5 | 5,600 |
| E7 | 475 | 44,000 |
| E8 | 22 | 6,300 |
| E9 | 48 | 43,000 |
| E10 | 30 | 2,800 |
| E11 | 38 | 6,500 |
| E12 | 260 | 2,100 |
| E15 | 242 | 28,100 |
| E16 | 2750 | 110,000 |
| E17 | 170 | 2,700 |
| E18 | 2.62 | 4,300 |
| E19 | 30 | 22,300 |
| E20 | 4.5 | 3,000 |
| E21 | 6600 | 310,200 |
| E22 | 153 | 55,000 |
| E23 | 325 | 3,300 |
| E25 | 180 | 22,000 |
| E27 | 12 | 3,200 |
| E28 | 17 | 2,600 |
| E29 | 22 | 12,800 |
| E30 | 1400 | — |
| E31 | 11.5 | 2,900 |
| E33 | 7.5 | 6,200 |
| E34 | 1400 | — |
| E35 | 8500 | 85,000 |

| Compound | [$^3$H]-oxo-M $IC_{50}$ (nm) | [$^3$H]-QNB $IC_{50}$ (nm) |
| --- | --- | --- |
| E36 | 19.5 | 6,750 |
| E37 | 130 | 58,000 |
| E38 | 180 | 14,490 |
| E39 | 14500 | — |
| E40 | 19.7 | 488 |
| E41 | 6.5 | 1,500 |
| E42 | 7.6 | 700 |
| E43 | 42.0 | 330 |
| E44 | 31.8 | 725 |

-continued

| Compound | [$^3$H]-oxo-M $IC_{50}$ (nm) | [$^3$H]-QNB $IC_{50}$ (nm) |
| --- | --- | --- |
| E45 | 36.0 | 360 |
| E46 | 1400 | 7,750 |
| E47 | 100 | 3,300 |
| E48 | 195 | 9,000 |
| E49 | 3.2 | 500 |
| E50 | 6.5 | 410 |
| E51 | 16.5 | 65,200 |
| E54 | 32 | 4,400 |

We claim:

1. A compound of formula (I) or a pharmaceutically acceptable salt thereof:

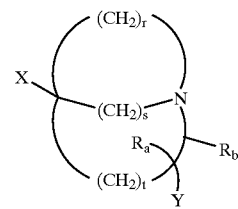

in which one of X and Y represents hydrogen and the other represents Z, where Z is a group

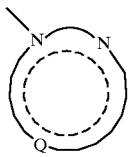

in which

Q represents a 3-membered divalent residue completing a 5-membered aromatic ring and comprises two nitrogen atoms with the remainder being a carbon atom, Q being optionally C-substituted by a group $R_1$ selected from the group consisting of halogen, CN, $OR_2$, $SR_2$, $N(R_2)$, $NHCOR_2$, $NHCOOCH_3$, $NHCOOC_2H_5$, $NHOR_2$, $N_3$, $NHNH_2$, $NO_2$, $COR_2$, $COR_3$, $C_{2-4}$ alkenyl, $C_{2-4}$ alkynyl, cyclopropyl and $C_{1-2}$ alkyl optionally substituted with a moiety selected from the group consisting of $OR_2$, $N(R_2)_2$, $SR_2$, $CO_2R_2$, $CON(R_2)_2$ and one, two or three halogen atoms, in which each $R_2$ is independently selected from the group consisting of hydrogen and $C_{1-2}$ alkyl and $R_3$ is selected from the group consisting of $OR_2$, $NH_2$ and $NHR_2$;

r represents an integer of 2 or 3, s represents an integer of 1 or 2 and t represents 0 or 1;

$R_a$ and $R_b$ each represent hydrogen or, when X is hydrogen, optionally together represent a bond;

with the provisos that (±) when Y is hydrogen s is 1 and (ii) when Z is tetrazol-1-yl and $R_1$ is absent or is H, unsubstituted $C_{1-2}$alkyl or $C_{2-4}$ alkynyl, then (r,s,t,) is not (2 1,0) or (2,2,0).

2. A compound according to claim 1 wherein $R_1$ is absent or hydrogen, methyl, ethyl, amino, cyano, azido, chloro, nitro, bromo or iodo.

3. A compound according to claim 1 wherein $R_1$ is γ to the position of the azabicyclic ring on Z.

4. A compound according to claim 1 wherein $R_a$ and $R_b$ are both hydrogen.

5. A pharmaceutical composition which comprises an effective amount of a compound according to claim 1 and a pharmaceutically acceptable carrier therefor.

6. A method of treatment and/or prophylaxis of dementia in mammals including humans, which comprises administering to a sufferer of said dementia an effective amount of a compound according to claim 1.

7. (±) 3-(5-methyltetrazol-2-yl)-1-azabicyclo[2.2.2]-octane, 3-(5-aminotetrazol-2-yl)-1-azabicyclo[2.2.2]octane, 3-(tetrazol-2-yl)-1-azabicyclo[2.2.2]octane, exo-3-(5-aminotetrazol-2-yl)-1-azabicyclo[3.2.1]octane, exo-3-(5-aminotetrazol-2-yl)-1-azabicyclo[2.2.1]heptane, exo-3-(tetrazol-2-yl)-1-azabicyclo [2.2.1]heptane, exo-3-(5-methyltetrazol-2-yl)-1-azabicyclo[2.2.1]heptane, exo-3-(tetrazol-2-yl)-1-azabicyclo[3.2.1]octane, exo-3-(5-ethyltetrazol-2-yl)-1-azabicyclo[2.2.1]heptane, endo-3-(5-aminotetrazol-2-yl)-1-azabicyclo[2.2.1]heptane, 5-(tetrazol-2-yl)-1-azabicyclo[3.2.1]octane, 5-(tetrazol-1-yl)-1-azabicyclo[3.2.1]octane, 5-(5-methyltetrazol-2-yl)-1-azabicyclo[3.2.1]octane, 5-(5-methyltetrazol-1-yl)-1-azabicyclo[3.2.1]octane, 5-(5-aminotetrazol-2-yl)-1-azabicyclo[3.2.1]octane, 5-(5-aminotetrazol-1-yl)-1-azabicyclo[3.2.1]octane, 3-(5-bromotetrazol-2-yl)-1-azabicyclo[2.2.2]octane, exo-3-(5-bromotetrazol-2-yl)-1-azabicyclo[2.2.1]heptane, exo-3-(5-chlorotetrazol-2-yl)-1-azabicyclo[2.2.1]heptane, exo-3-(5-iodotetrazol-2-yl)-1-azabicyclo[2.2.1]heptane, 3-(5-chlorotetrazol-2-yl)-1-azabicyclo[2.2.2]octane, 3-(5-iodotetrazol-2-yl)-1-azabicyclo[2.2.2]octane, 3-(5-cyanotetrazol-2-yl)-1-azabicyclo[2.2.2]octane, 5-(5-chlorotetrazol-2-yl)-1-azabicyclo[3.2.1]octane, 5-(5-bromotetrazol-2-yl)-1-azabicyclo[3.2.1]octane, or a pharmaceutically acceptable salt of any of the foregoing compounds.

8. A compound according to claim 1, wherein (r,s,t) is (2,2,0), (3,1,0), (2,1,0), (2,1,1), or (3,1,1).

* * * * *

UNITED STATES PATENT AND TRADEMARK OFFICE
CERTIFICATE OF CORRECTION

PATENT NO. : 5,981,545
DATED : November 9, 1999
INVENTOR(S) : S.M. Jenkins, et al.

It is certified that error appears in the above-identified patent and that said Letters Patent is hereby corrected as shown below:

Column 48, line 42, "$N(R_2$" should be replaced with $- N(R_2)_2$-;
line 57, "(±)" should be replaced with -(i)- ; and
Line 60, "(2 1,0)" should be replaced with -(2,1,0)-.

Signed and Sealed this

Ninth Day of May, 2000

Attest:

Q. TODD DICKINSON

*Attesting Officer*  *Director of Patents and Trademarks*